United States Patent [19]

Zipperer et al.

[11] Patent Number: 5,290,806
[45] Date of Patent: Mar. 1, 1994

[54] 4-(4-TERT-BUTYLPHENYL) CYCLOHEXYLAMINES, AND FUNGICIDES CONTAINING SAME

[75] Inventors: Bernhard Zipperer, Dirmstein; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 85,255

[22] Filed: Jul. 2, 1993

Related U.S. Application Data

[63] Continuation of Ser. No. 860,290, Mar. 25, 1992, abandoned, which is a continuation of Ser. No. 662,625, Feb. 28, 1991, abandoned.

[30] Foreign Application Priority Data

Mar. 6, 1990 [DE] Fed. Rep. of Germany ....... 4006937

[51] Int. Cl.$^5$ ................... A01N 33/12; C07C 255/00; C07C 211/00
[52] U.S. Cl. ..................... 514/643; 514/647; 558/408; 558/418; 558/422; 564/284; 564/285; 564/287; 564/288; 564/289; 564/307
[58] Field of Search ............... 514/643, 647; 558/408, 558/418, 422; 564/284, 285, 287, 288, 289, 307

[56] References Cited

U.S. PATENT DOCUMENTS 2,967,125 1/1961 Carlson .
3,981,766 9/1976 Pechhold .
4,897,425 1/1990 Zipperer et al. .
4,968,676 11/1990 Zipperer et al. .

FOREIGN PATENT DOCUMENTS 0259977 3/1988 European Pat. Off. .
0019829 10/1967 Japan ................... 564/307

OTHER PUBLICATIONS

The Journal of Organic Chemistry, vol. 48, 1983, pp. 3412-3422, R. O. Hutchins et al., "Stereoselective Reductions of Substituted Cyclohexyl and Cyclopentyl Carbon-Nitrogen $\pi$ Systems with Hydride Reagents[1]".

Primary Examiner—Alan Siegel
Attorney, Agent, or Firm—Oblon, Spivak, McClelland, Maier & Neustadt

[57] ABSTRACT 4-4(tert-butylphenyl)-cyclohexylamines and quaternary ammonium salts thereof of the formulae

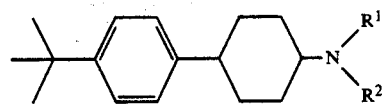

and

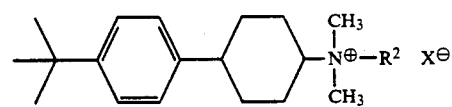

where
R$^1$ is hydrogen, alkyl or alkenyl,
R$^2$ is alkyl, haloalkyl, hydroxyalkyl, cycloalkyl, alkylcycloalkyl, bicycloalkyl, alkenyl, unsubstituted or mon- to trisubstituted phenyl, or unsubstituted or mono- to trisubstituted phenylalkyl,
X$^\ominus$ is a plant-tolerated acid anion,
and their plant-tolerated acid addition salts, and fungicides containing these compounds.

7 Claims, No Drawings

4-(4-TERT-BUTYLPHENYL) CYCLOHEXYLAMINES, AND FUNGICIDES CONTAINING SAME

This application is a continuation of application Ser. No. 07/860,290filed on Mar. 25, 1992, now abandoned which is a continuation of Ser. No. 07/662,625, filed Feb. 28, 1991, now abandoned.

The present invention relates to novel 4-(4-tert-butylphenyl)cyclohexylamines and acid-addition salts and quaternary salts thereof, to a process and intermediates for the preparation thereof, to the use thereof as fungicides, to fungicides, and to a method of controlling harmful fungi using these active ingredients.

The compound trans-4-tert-butyl-N-benzylcyclohexylamine is known (J. Org. Chem. 48 (1983) 3412–3422), but nothing is known on its fungicidal action 4-(Cyclohexylmethyl)cyclohexylamine and its N,N-dimethyl derivative are known as fungicides (U.S. Pat. No. 3,981,766), but their fungicidal action is unsatisfactory.

1-[4-(4-tert-Butylphenyl)cyclohexyl]-2,6-dimethylmorpholine has been described as a fungicide (EP 259 977), but its efficacy is poor in some areas of application, in particular at low application rates and concentrations.

Fungicidal cyclohexylamines are disclosed in DE 36 40 247. Their fungicidal action is good, but their plant compatibility is unsatisfactory, particularly at relatively high application rates.

We have now found that 4-(4-tert-butylphenyl)cyclohexylamines and the quaternary ammonium salts thereof, of the formulae

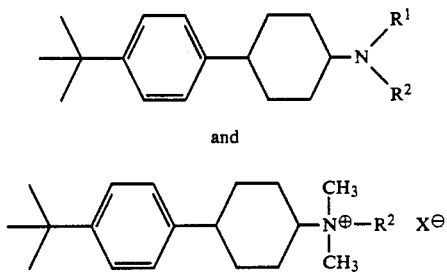

and where
$R^1$ is hydrogen, $C_1$–$C_6$-alkyl or $C_3$–$C_6$-alkenyl,
$R^2$ is $C_1$–$C_{12}$-alkyl, $C_1$–$C_{12}$-haloalkyl, $C_1$–$C_{12}$-hydroxyalkyl, $C_3$–$C_{12}$-cycloalkyl, $C_4$–$C_{12}$-alkylcycloalkyl, $C_7$–$C_{12}$-bicycloalkyl, $C_3$–$C_{12}$-alkenyl, unsubstituted, monosubstituted disubstituted or trisubstituted phenyl, or unsubstituted, monosubstituted, disubstituted or trisubstituted phenyl($C_1$–$C_3$)-alkyl, possible substituents in each case being identical or different $C_1$–$C_4$-alkyl, $C_1$–$C_4$-alkoxy, $C_1$–$C_4$-haloalkyl, $C_1C_4$-haloalkoxy, halogen, cyano, hydroxyl or nitro groups, with the proviso that $R^1$ and $R^2$ are not simultaneously $C_1$–$C_4$-alkyl,
$X^\ominus$ is a plant-compatible acid anion,
and the plant-compatible acid addition salts thereof, have a strong fungicidal action and surprisingly good plant compatibility $R^1$ is, for example, hydrogen, straight-chain or branched $C_1$–$C_6$-alkyl, in particular $C_1$–$C_4$-alkyl, such as methyl, ethyl, n-propyl, isopropyl, n-butyl, isobutyl, sec-butyl, tert-butyl, n-pentyl, isopentyl, tert-pentyl, n-hexyl, isohexyl or neohexyl, or straight-chain or branched $C_2$–$C_6$-alkenyl, such as 2-propen-1-yl-, cis- or trans-2-buten-1-yl, 2-methyl-2-propen-1-yl, 3-buten-2-yl or 3-methyl-2-buten-1-yl.

$R^2$ is, for example, straight-chain or branched $C_1$–$C_{12}$-alkyl, in particular $C_1$–$C_4$-alkyl, such as methyl, ethyl, n-propyl, isopropyl, n-butyl, isobutyl, sec-butyl, tert-butyl, n-pentyl, isopentyl, neopentyl, n-hexyl, neohexyl, n-heptyl, n-octyl, 2-ethylhexyl, n-nonyl, n-decyl, n-undecyl or n-dodecyl; $C_1$–$C_{12}$-haloalkyl such as chloromethyl, bromomethyl, iodomethyl, 2-chloroethyl, 4-chloro-1-butyl, 3-chloro-1-butyl-, 3-chloro-2-methyl-1-propyl, 5-chloro-1-pentyl or 6-chloro-1-hexyl; $C_1$–$C_{12}$-hydroxyalkyl, such as 2-hydroxyethyl, 2-hydroxy-1-propyl, 6-hydroxy-1-hexyl, 8-hydroxy-1-octyl or 10-hydroxy-1-decyl; $C_3$–$C_{12}$-cycloalkyl such as cyclopropyl, cyclobutyl, cyclopentyl, oyclohexyl, cycloheptyl, cyclodecyl or cyclododecyl; $C_4$–$C_{12}$-alkylcycloalkyl such as methylcyclopropyl, methylcyclopentyl, 2-, 3- or 4-methylcyclohexyl, 2-, 3- or 4-ethylcyclohexyl, 4-isopropylcyclohexyl, 4-tert-butylcyclohexyl, 2,2-, 3,3- or 4,4-dimethylcyclohexyl, 2,6-dimethylcyclohexyl or 3,3,5,5-tetramethylcyclohexyl; $C_7$–$C_{12}$-bicycloalkyl such as bicyclo[2.2.1]hept-2-yl, 1,7,7-trimethylbicyclo[2.2.1]hept-2-yl, bicyclo[4.4.0]dec-2-yl or bicyclo[4.4.0]dec-3-yl; phenyl, $C_1$–$C_4$-alkylphenyl, mono-, di- or trimethylphenyl, ethylphenyl, isopropylphenyl, tert-butylphenyl, $C_1$–$C_4$-alkoxyphenyl, mono-, di- or trimethoxyphenyl, n- or tertphenyl, $C_1$–$C_4$-haloalkylphenyl, $C_1$–$C_4$-haloalkoxybutoxy phenyl, trifluoromethylphenyl, difluoromethoxyphenyl, trifluoromethoxyphenyl, tetrafluoroethoxyphenyl, cyanophenyl, nitrophenyl, mono-, di- or trichlorophenyl, mono-, di- or trifluorophenyl, chlorofluorophenyl, bromophenyl, aryl($C_1$–$C_3$)alkyl, such as benzyl, $C_1$–$C_4$-alkylbenzyl, mono-, di- or trimethylbenzyl, tert-butylbenzyl, halobenzyl, fluorobenzyl, mono-, di- or trichlorobenzyl, $C_1$–$C_4$-alkoxybenzyl, mono-, di- or trimethoxybenzyl, cyanobenzyl, nitrobenzyl, 2-phenylethyl, 2-(methoxyphenyl)ethyl,2-(chlorophenyl)ethyl,2-(fluorophenyl)ethyl, 2-(tert-butylphenyl)ethyl, 3-phenylpropyl, 3-(chlorophenyl)propyl or 3-(fluorophenyl)propyl.

$X^\ominus$ is an inorganic or organic acid anion, for example chloride, bromide, iodide, sulfate, hydrogen sulfate, phosphate, hydrogen phosphate, dihydrogen phosphate, nitrate, tetrafluoroborate; formate, acetate, oxalate, methanesulfonate, benzenesulfonate, p-toluenesulfonate or dodecylbenzenesulfonate.

Examples of acids for the preparation of the acid-addition salts are mineral acids, hydrochloric acid, sulfuric acid, nitric acid, formic acid, alkylcarboxylic acids, such as acetic acid, propionic acid, oxalic acid, sulfonic acids, such as methanesulfonic acid, benzenesulfonic acid, p-toluenesulfonic acid and dodecylbenzenesulfonic acid.

The novel compounds of the formulae 1 and 2 can exist in two diastereomeric forms, namely as cis-1,4- and as trans-1,4-disubstituted cyclohexane Depending on the preparation method, they are obtained either as pure diastereomers or as diastereomer mixtures. If desired, the latter can be resolved to give pure diastereomers by generally known methods, for example by chromatography or fractional crystallization. The present invention relates both to the pure diastereomers and to mixtures thereof.

In some of the radicals $R^2$ according to the invention, further isomers can occur in addition to the abovementioned cis/trans isomerism. Depending on the nature of R², these isomers may be enantiomers or diastereomers. Here too, the diastereomeric compounds can be resolved by conventional methods, for example by chromatography or crystallization All isomeric compounds and mixtures thereof with one another are included in the present invention. The pure diastereomers or enantiomers thereof are suitable for use of the novel amines as fungicides Preference is given to The present invention also relates to a process for the preparation of the novel amines of the formula 1.

a) These amines can be prepared, for example, by reacting an amine of the formula

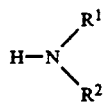 3 where
$R^1$ hydrogen, $C_1$–$C_6$-alkyl or $C_3$–$C_6$-alkenyl and
$R^2$ is $C_1$–$C_{12}$-alkyl, with the proviso that $R^1$ and $R^2$ are not simultaneously $C_1$–$C_4$-alkyl, or is $C_1$–$C_{12}$-haloalkyl, $C_1$–$C_{12}$-hydroxyalkyl, $C_3$–$C_{12}$-cycloalkyl, $C_4$–$C_{12}$-alkylcycloalkyl, $C_7$–$C_{12}$-bicycloalkyl, $C_3$–$C_{12}$-alkenyl, unsubstituted, monosubstituted, disubstituted or trisubstituted phenyl, or unsubstituted, monosubstituted, disubstituted or trisubstituted phenyl($C_1$–$C_3$)-alkyl, possible substituents being in each case identical or different $C_1$–$C_4$-alkyl, $C_1$–$C_4$-alkoxy, $C_1$–$C_4$-haloalkyl, $C_1$–$C_4$-haloalkoxy, halogen, cyano, hydroxyl or nitro groups, with 4-(4-tert-butylphenyl)cyclohexanone, and reducing the imine (in the case where $R^1$ is hydrogen) or enamine (in the case where $R^1$ is not hydrogen) produced as a reaction product, either directly or after isolation, using a reducing agent to give an amine of the formula 1.

It is advantageous to remove from the reaction mixture the water of reaction liberated on reaction of an amine of the formula 3 in which $R^1$ and $R^2$ are as defined above with 4-(4-tert-butylphenyl)cyclohexanone. This can be effected, for example, by adding a dehydrating agent or by azeotropic distillation. Examples of suitable dehydrating agents are salts which are free of or low in water of hydration, such as sodium sulfate, magnesium sulfate, zinc sulfate, calcium chloride or molecular sieves. The reaction is carried out in the presence or absence of an inert organic solvent and in the presence or absence of a catalytic amount of acid. Suitable solvents are hydrocarbons, such as cyclohexane, benzene, toluene or xylenes, chlorinated hydrocarbons, such as dichloromethane or 1,2-dichloroethane, or ethers, such as diethyl ether, methyl tert-butyl ether, tetrahydrofuran or dioxane. Examples of suitable acids are mineral acids, such as sulfuric acid or phosphoric acid, or sulfonic acids, such as methanesulfonic acid, benzenesulfonic acid or p-toluenesulfonic acid. The amount of acid necessary is, for example, from 0 to 10 mol-%, preferably from 0 to 1 mol-%, based on the amine of the formula 3. The reaction can be carried out at room temperature or at elevated temperature, for example up to the boiling point of the particular solvent. If the reaction temperature which is necessary cannot be achieved under atmospheric pressure or if the reaction proceeds only slowly, the reaction can be carried out in an autoclave (with or without a solvent) at elevated temperature under the inherent pressure of the reaction mixture. If the water of reaction produced is removed from the reaction mixture by azeotropic distillation, the reaction is carried out at the boiling point of the particular solvent. Preferred solvents here are aromatic hydrocarbons, such as benzene, toluene or xylenes.

The unsaturated nitrogen compound (imine or enamine) produced on reaction of an amine of the formula 3 where $R^1$ and $R^2$ are as defined above with 4-(4-tert-butylphenyl)cyclohexanone can be reduced by conventional methods to give an amine of the formula 1. Specific examples of preferred reducing agents are hydrogen, formic acid, or complex hydrides such as sodium borohydride or sodium cyanoborohydride. Particular preference is given to hydrogen in the presence of a metallic catalyst. Examples of suitable catalysts are finely divided metals, such as Raney nickel or Raney cobalt, and noble metals, such as palladium or platinum, with or without a solid carrier. The hydrogenation using hydrogen can be carried out with or without pressure (cf., for example, Houben-Weyl, Methoden der Organischen Chemie, Volume 11/1, pp. 602 ff, G. Thieme Verlag, Stuttgart, 1957). It is occasionally advantageous to prepare the amine of the formula 1 in one step from an amine of the formula 3 and 4-(4-tert-butylphenyl)cyclohexanone.

A known process for this purpose in which the reducing agent is formic acid is the reductive amination by the Leuckardt-Wallach method (cf., for example, Houben-Weyl, Methoden der Organischen Chemie, Volume 11/1, pp. 648 ff, G. Thieme Verlag, Stuttgart, 1957). Another process, which is particularly advantageous for laboratory scale syntheses, uses sodium cyanoborohydride as the reducing agent (cf., for example, C. F. Lane, Synthesis 1975, 135). The combination of sodium cyanoborohydride and anhydrous zinc chloride has proven particularly expedient (cf. S. Kim et al., J. Org. Chem. 50 (1985) 1927).

In this process, the NaBH₃CN:ZnCl₂ molar ratio can be, for example, from 1:2 to 1:0.5, preferably 1:0.5. As far as the amount of NaBH₃CN employed is concerned, either the amine component 3 or the ketone component can be used in an equimolar amount; an excess of the other component may occasionally be advantageous in order to accelerate or complete the reaction The reaction is preferably carried out in a lower alcohol, such as methanol, ethanol, n-propanol or isopropanol, particularly preferably in methanol, as solvent, at between 0° C. and the boiling point of the particular solvent. The reaction is preferably carried out at room temperature.

The 4-(4-tert-butylphenyl)cyclohexanone used as starting material is novel. It can be prepared from known, commercially available 4-phenylcyclohexanone by Friedel-Crafts alkylation of the phenyl ring. Examples of alkylating agents are tert-butyl chloride or bromide, tert-butanol or 2-methylpropene (cf., for example, Houben-Weyl, Methoden der Organischen Chemie, Vol. 5/2b, pp. 154 ff., pp. 179 ff., G. Thieme Verlag, Stuttgart, 1981). Preference is given to 2-methylpropene in the presence of a mineral acid, for example sulfuric acid or phosphoric acid, or in the presence of a Lewis acid, such as aluminum trichloride, iron(III) chloride or boron trifluoride. Suitable solvents are in particular chlorinated hydrocarbons, especially dichloromethane, tetrachloromethane, and 1,2-dichloroethane. The tert-butylation of the 4-phenylcyclohexanone can be carried out at room temperature or below, preferably at from 0° to 20° C.

The amines of the formula 3 where $R^1$ and $R^2$ are as defined above are known compounds and those which are not commercially available can be prepared by known processes.

The amines prepared by the above-described process, where $R^1$ and $R^2$ are as defined above, are generally mixtures of the two possible stereoisomers containing a cis- or trans-1,4-disubstituted cyclohexane ring. These cis/trans mixtures may, if desired, be resolved into their constituents by known methods, for example by chromatography or fractional crystallization.

b) A further process allows the targeted preparation of cis- or trans-4-(4-tert-butylphenyl)cyclohexylamines of the formula 1 where $R^1$ is hydrogen and $R^2$ is $C_1$–$C_{12}$-alkyl, $C_1$–$C_{12}$-haloalkyl, $C_1$–$C_{12}$-hydroxyalkyl, $C_3$–$C_{12}$-cycloalkyl, $C_4$–$C_{12}$-alkylcycloalkyl, $C_7$–$C_{12}$-bicycloalkyl, $C_3$–$C_{12}$-alkenyl, unsubstituted, monosubstituted, disubstituted or trisubstituted phenyl, or unsubstituted, monosubstituted, disubstituted or trisubstituted phenyl($C_1$–$C_3$)alkyl, possible substituents in each case being identical or different $C_1$–$C_4$-alkyl, $C_1$–$C_4$-alkoxy, $C_1$–$C_4$-haloalkyl, $C_1$–$C_4$-haloalkoxy, halogen, cyano, hydroxyl or nitro groups This process comprises first converting 4-(4-tert-butylphenyl)cyclohexanone into 4-(4-tert-butylphenyl)-cyclohexanone oxime by conventional methods using hydroxylamine or a hydroxylamine salt, and subsequently reducing this oxime using sodium in ethanol (cf., for example, Chem. Ind. (London) 1972, 683). The trans-4-(tert-butylphenyl)cyclohexylamine obtained is then reacted in a further step with a carbonyl compound of the formula

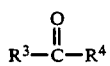    4 where $R^3$ and $R^4$ are such that the radical

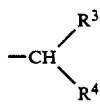

corresponds in its entirety to $R^2$ as defined above, and the imine formed is reduced, directly or after isolation, using a reducing agent to give the amine of the formula 1.

If 4-(4-tert-butylphenyl)cyclohexanone oxime is reduced, for example, using hydrogen, a mixture of cis- and trans-4-(4-tert-butylphenyl)cyclohexylamine is obtained, which can be resolved into the pure cis- and trans-isomers by conventional methods, for example by chromatography, distillation or fractional crystallization of an acid-addition salt with subsequent liberation of the base The two isomers can then be reacted separately with a carbonyl compound of the formula

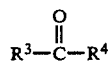    4

$R^3$ and $R^4$ are as defined above to give the pure cis- where and trans-configured amines of the formula 1.

It is of course also possible to react the mixture of cis- and trans-4-(4-tert-butylphenyl)cyclohexylamines with a carbonyl compound of the formula 4 and to resolve the resultant isomer mixture of amines of the formula 1 into its constituents, for example by chromatography or crystallization.

A further way of preparing a cis/trans mixture of 4-(4-tert-butylphenyl)cyclohexylaminescomprises alkylating cis/trans-4-phenylcyclohexylamine using 2-methylpropene in the presence of an at least equimolar amount of mineral acid, for example sulfuric acid. Preferred solvents are chlorinated hydrocarbons, e.g. dichloromethane, tetrachloromethane or 1,2-dichloroethane. The alkylation can be carried out at room temperature or below, preferably at from 0° to 20° C.

The 4-phenylcyclohexylamine used as a starting material is known. It can be prepared, for example, by hydrogenating 4-aminobiphenyl (R. Egli, C.H. Eugster, Helv. Chim. Acta 58 (1975) 2321) or 4-phenylcyclohexanone oxime (Nightingale et al., J. Org. Chem. 17 (1952) 1017).

The carbonyl compounds of the formula 4 which are required for process b) are common chemicals, and those which are not commercially available can be prepared by conventional methods.

The reaction conditions described in detail for process a) also apply similarly to process b).

The above-described process b) gives the amines of the formula 1 where $R^1$ is hydrogen. These secondary amines can, if desired, be converted into tertiary amines of the formula 1 where $R^1$ is $C_1$–$C_6$-alkyl or $C_3$–$C_6$-alkenyl by known alkylation reactions.

If the alkylating agent used is a methyl compound of the formula

$CH_3$—A    5 where A is a nucleofugic leaving group, e.g. chlorine, bromine, iodine, $O-SO_2-OCH_3$, $O-SO_2-CH_3$ or $O\text{-}SO_2-p-C_6H_4-CH_3$, and the alkylating agent is employed in excess, 4-(4-tert-butylphenyl)cyclohexylammonium salts of the formula 2 where $R^2$ is as defined above are obtained This quaternization can be carried out in the presence or absence of a diluent Examples of suitable diluents are alcohols, such as methanol, ethanol, n- or isopropanol, n-butanol or cyclohexanol, ethers, such as diethyl ether, methyl tert-butyl ether, tetrahydrofuran or dioxane, esters, such as methyl acetate or ethyl acetate, nitriles, such as acetonitrile or propionitrile, nitro compounds, such as nitromethane or nitrobenzene, or other solvents which are inert in this reaction The alkylation is preferably carried out using two to 6 times the molar amount of alkylating agent of the formula 5 and at from 20° to 200° C. The reaction is expediently carried out at the boiling point of the particular diluent, or, if none is used, of the particular alkylating agent.

It is occasionally advantageous to carry out the quaternization in the presence of an auxiliary base, which can be added in excess or in an equimolar amount, based on the amine 1 to be alkylated. The use of a base which is insoluble in the reaction medium, for example sodium carbonate, potassium carbonate or calcium carbonate, is particularly advantageous The reaction product obtained is a 4-(4-tertbutylphenyl)cyclohexylammonium salt of the formula

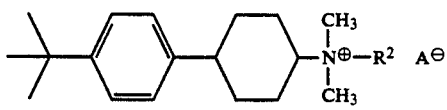

where $R^2$ and A are as defined above. If necessary, the anion $A^\ominus$ can be replaced by another, plant-compatible acid anion by conventional methods, for example by ion exchange chromatography.

up in water, rendered alkaline using concentrated NaOH and extracted several times with methyl tert-butyl ether. The organic phase is dried over $Na_2SO_4$, freed from solvent and then distilled under reduced pressure After an initial fraction comprising principally 4-tert-butylcyclohexylamine, 19.3 g (75% of theory) of the title compound are obtained at 210°-212° C./0.2 mbar as a colorless, viscous oil. According to GC and $^1H$—NMR analysis, it is a cis/trans mixture in the ratio 2:3.

SCHEME 1

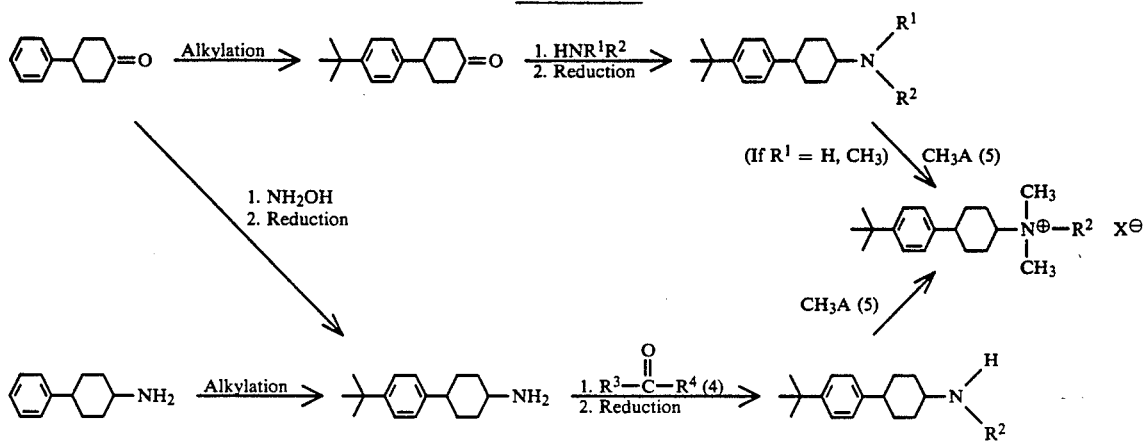

The examples below are intended to illustrate the preparation of the compounds according to the invention in greater detail.

EXAMPLE 1

5 4-(4-tert-Butylphenyl)cyclohexanone 170.5 g (1.74 mol) of concentrated sulfuric acid are added dropwise with stirring and cooling at from 0° to 5° C. to a solution of 50 g (0.287 mol) of 4-phenylcyclohexanone in 600 ml of dichloromethane. 19.5 g (0.35 mol) of isobutylene (2-methylpropene) gas are passed into this mixture over the course of 15 to 20 minutes at from 10° to 15° C. The mixture is stirred at room temperature (20° C.) for a further one hour and 250 ml of water are then added dropwise with ice cooling. The organic phase is separated off, washed neutral with water, 10% strength NaOH and again with water, dried over $Na_2SO_4$ and evaporated under reduced pressure. The residue is recrystallized from n-pentane, to give 50.7 g (76% of theory) of colorless $^1H$—NMR (CDCl$_3$): δ=7.35 (d, 2H), 7.18 (d, 2H), 3.00 (br, t, 1H), 2.50 (m, 4H), 2.21 (m, 2H), 1.95 (m, 2H), 1.30 (s, 9H).

IR (KBr): ν=2965, 2944, 2867, 1710, 1418, 1160, 832, 808, 570 cm$^{-1}$:

EXAMPLE 2

4-trans-tert-Butyl-4,-cis/trans-(4-tert-butylphenyl)-N,N-dicyclohexylamine (Compound No. 62)

16.1 g (0.07 mol) of 4-(4-tert-butylphenyl)cyclohexanone, 21.7 g (0.14 mol) of trans-4-tert-butylcyclohexylamine and 4.8 g (0.035 mol) of anhydrous zinc chloride are dissolved in 250 ml of methanol. 4.4 g (0.07 mol) of sodium cyanoborohydride are introduced into the solution in portions. The mixture is stirred at room temperature for 24 hours, and the majority of the solvent is then stripped off under reduced pressure. The residue taken

| | | | |
|---|---|---|---|
| $C_{26}H_{43}N$ (369.1) Calc. | C 84.48 | H 11.73 | N 3.79 |
| Found | C 84.5 | H 11.7 | N 3.6 |

EXAMPLE 3

Resolution of 4-trans-tert-butyl-4'-cis/trans-4-(tert-butylphenyl)-N,N-dicyclohexylamine 8.0 g of a cis/trans isomer mixture obtained as in Example 2 are resolved by chromatography on a 30×3 cm silica gel column (Macherey & Nagel, 0.04–0.06 mm) using cyclohexane/ethyl acetate (4:1) at 0.1 bar of nitrogen. The 4-trans-tert-butyl-4'-cis-(4-tert-butylphenyl)-N,N-dicyclohexylamine is eluted first as a colorless solid of melting point 54°-56° C. (ethanol). The relative stereochemistry was determined by $^1H$— and $^{13}C$—NMR spectroscopy.

$^1H$—NMR (CDCl$_3$): inter alia δ=3.00 (m, 1'—H$_{eq}$), 2.55 (m, 1—H$_{ax}$), 2,40 (4'—H$_{ax}$).

$^{13}C$—NMR (CDCl$_3$): inter alia δ=54.04 (C—1'), 43.69 (C-4'), 34.86 (C—2'(6')), 33.39 (C—3'(5')).

After a mixed fraction (0.8 g), 4-trans-tert-butyl-4,-trans-(4-tert-butylphenyl)-N,N-dicyclohexylamine is obtained, initially as a pale yellow oil, which crystallizes from acetonitrile. Colorless crystals, melting point 112°-113° C.

$^1H$—NMR (CDCl$_3$): inter alia δ=2.67 (br.m, 1'—H$_{ax}$), 2.50 (br. m, 1—H$_{ax}$+4'H$_{ax}$).

$^{13}C$—NMR (CDCl$_3$): inter alia δ=48.42 (C-1'), 42.69 (C—4'), 30.98 (C-2'(6')), 28.30 (C-3'(5')).

EXAMPLE 4

N,N-Dimethyl-4-trans-tert-butyl-4,-cis/trans-(4-tert-butylphenyl)-N,N-dicyclohexylammonium iodide 7.4 g (0.02 mol) of 4-trans-tert-butyl-4'-cis/ trans-(4-tert-butylphenyl)-N,N-dicyclohexylamine (Example 2), 11.4 g (0.08 mol) of methyl iodide and 10.2 g of sodium carbonate (0.10 mol) are refluxed for 6 hours in 50 ml of ethanol After cooling, the mixture is filtered, the filtrate is evaporated to dryness under reduced pressure, and the oily residue is boiled with 50 ml of ethyl acetate The mixture is left to stand overnight, and the precipitate is filtered off with suction, washed with ice-cold acetone and dried at 50° C. under reduced pressure, to give 6.7 g (62% of theory) of quaternary salt as colorless crystals of melting point 184°–185° C.

EXAMPLE 5 cis/trans-4-(4-tert-Butylphenyl)cyclohexylamine 165 g of concentrated $H_2SO_4$ (1.68 mol) are added dropwise to 52.5 g (0.30 mol) of well cooled 4-phenylcyclohexylamine (cis/trans ratio of about 2:3) at from 0 to 5° C. 1,000 ml of dichloromethane diluent are added, and 21.8 g (0.39 mol) of isobutylene gas are passed in over the course of 20 minutes at from 10° to 15° C. After one hour at 20° C., 250 ml of water are added dropwise with ice cooling. The aqueous phase is extracted twice with $CH_2Cl_2$. The combined organic phases are stirred vigorously with 1 l of 10 percent strength by weight NaOH, then with water, dried over $Na_2SO_4$ and evaporated under washed reduced pressure. The crude amine, which is about 70% pure according to gas chromatography, is dissolved in 500 ml of ether and precipitated as the hydrochloride by passing in HCl gas with ice cooling to give 35.3 g (44.5% of theory) of a yellowish crystal powder which decomposes above 240° C.

IR (KBr): $\nu = 2956, 2932, 2868, 1607, 1510, 1448, 1362, 1268, 831, 574$ cm$^{-1}$.

The free base is obtained therefrom by adding aqueous ammonia solution, extracting the mixture with methyl tert-butyl ether, and drying and evaporating the organic phase to give a colorless oil (cis/trans mixture). Characteristic NMR data (CDCl$_3$): cis-4-(4-tertbutylphenyl)cyclohexylamine: $\delta 1-H_{eq} = 3.19$; $\gamma$ C-1 = 45.3 ppm.

trans-4-(4-tert-butylphenyl)cyclohexylamine: $\delta$ 1-$H_{ax} = 2.70$; $\delta$ C-1 = 50.2 ppm.

EXAMPLE 6

N-Benzyl-N-4-(4-tert-butylphenyl)cyclohexylamine (Compound No. 104)

A solution of 11.6 g (0.05 mol) of 4-(4-tertbutylphenyl)cyclohexylamine (cis/trans mixture) and 6.4 g (0.06 mol) of freshly distilled benzaldehyde in 200 ml of toluene is treated with 14.2 g (0.10 mol) of sodium sulfate and stirred at room temperature overnight. After filtration, the toluene is stripped off and replaced by ethanol. 2.7 g (0.07 mol) of sodium borohydride are then added, the mixture is refluxed for one hour and evaporated to dryness, and the residue is partitioned between water and methyl tert-butyl ether. The organic phase is washed with water, dried over sodium sulfate and evaporated, and the residue is subjected to incipient distillation at 2 mbar up to 200° C. to give 9 g (56% of theory) of a pale reddish resin, a 2:1 trans/cis isomer mixture according to $^1$H—NMR and gas chromatography.

IR (film): $\nu = 2961, 2927, 2862, 1461, 1452, 1362, 827, 736, 698, 572$ cm$^{-1}$.

| $C_{23}H_{31}N$ (321.1) | | | |
|---|---|---|---|
| Calc. | C 85.92 | H 9.72 | N 4.36 |
| Found | C 85.5 | H 9.9 | N 4.1 |

The following compounds are prepared by measures similar to these Examples:

| No. | R$^1$ | R$^2$ | Physical data |
|---|---|---|---|
| 1 | H | Methyl | |
| 2 | H | Ethyl | |
| 3 | H | 1-Propyl | |
| 4 | H | 2-Propyl | |
| 5 | H | 1-Butyl | bp. 220–224° C./2 mbar (cis/trans = 1:2) |
| 6 | H | 2-Butyl | |
| 7 | H | tert.-Butyl | |
| 8 | H | 2-Methyl-1-propyl | |
| 9 | H | 1-Pentyl | |
| 10 | H | 2-Methyl-1-butyl | |
| 11 | H | 2-Methyl-1-pentyl | |
| 12 | H | 2-Ethyl-1-butyl | |
| 13 | H | 2,2-Dimethyl-1-propyl | |
| 14 | H | 3,3-Dimethyl-1-butyl | |
| 15 | H | 3-Methyl-1-butyl | resin (cis/trans = 1:2) |
| 16 | H | 1-Hexyl | |
| 17 | H | 2-Methyl-1-hexyl | |
| 18 | H | 2-Ethyl-1-hexyl | |
| 19 | H | 2,4,4-Trimethyl-1-pentyl | |
| 20 | H | 1-Heptyl | |
| 21 | H | 1-Octyl | |
| 22 | H | 1-Nonyl | |
| 23 | H | 1-Decyl | |
| 24 | H | 1-Undecyl | |
| 25 | H | 1-Dodecyl | |
| 26 | H | 2-Propen-1-yl | |
| 27 | H | 2-Buten-1-yl | |
| 28 | H | 2-Penten-1-yl | |
| 29 | H | 2-Hexen-1-yl | |
| 30 | H | 3-Methyl-2-buten-1-yl | |
| 31 | H | 2,3-Dimethyl-2-buten-1-yl | |
| 32 | H | 2-Hydroxyethyl | |

-continued

| No. | R¹ | R² | Physical data |
|-----|----|----|---------------|
| 33 | H | 6-Hydroxy-1-hexyl | |
| 34 | H | 3-Chloro-1-butyl | |
| 35 | H | 4-Chloro-1-butyl | |
| 36 | H | 3-Chloro-2-methyl-1-propyl | |
| 37 | H | Cyclopropyl | |
| 38 | H | Cyclobutyl | |
| 39 | H | Cyclopentyl | bp. 180–186° C./0.5 mbar (cis/trans = 1:2) |
| 40 | H | Cyclohexyl | bp. 167–170° C./0.4 mbar (cis/trans = 1:2) |
| 41 | H | Cycloheptyl | |
| 42 | H | Cyclooctyl | |
| 43 | H | Cyclodecyl | |
| 44 | H | Cyclododecyl | |
| 45 | H | 1-Methylcyclopropyl | |
| 46 | H | 1-Methylcyclopentyl | |
| 47 | H | 1-Methylcyclohexyl | |
| 48 | H | 2-Methylcyclohexyl | |
| 49 | H | 3-Methylcyclohexyl | |
| 50 | H | 4-Methylcyclohexyl | IR: 2949, 2923, 2865, 2851, 1447, 1363, 1112, 826, 571 |
| 51 | H | 2,2-Dimethylcyclohexyl | |
| 52 | H | 3,3-Dimethylcyclohexyl | |
| 53 | H | 4,4-Dimethylcyclohexyl | |
| 54 | H | 2,6-Dimethylcyclohexyl | |
| 55 | H | 3,3,5-Trimethylcyclohexyl | |
| 56 | H | 3,3,5,5-Tetramethylcyclohexyl | |
| 57 | H | 4-Ethylcyclohexyl | |
| 58 | H | 4-Propylcyclohexyl | |
| 59 | H | 4-Isopropylcyclohexyl | Hydrochloride: IR: 2951, 2865, 2794 2734, 1462, 1385, 1363, 827, 572 |
| 60 | H | 4-tert.-Butylcyclohexyl | |
| 61 | H | cis-4-tert.-Butylcyclohexyl | |
| 62 | H | trans-4-tert.-Butylcyclohexyl | 4'-cis: Fp. 54–56° C.; 4'-trans: mp. 112–113° C. |
| 63 | H | 4 tert.-Amylcyclohexyl | |
| 64 | H | Bicyclo[2.2.1]-hept-2-yl | |
| 65 | H | 1,7,7-Trimethyl-bicyclo[2.2.1]-hept-2-yl | |
| 66 | H | Bicyclo[4.4.0]dec-2-yl | |
| 67 | H | Bicyclo[4.4.0]dec-3-yl | IR: 2923, 2856, 1464, 1447, 1362, 1269, 1111, 826, 571 resin (cis/trans = 1:2) |
| 68 | H | 2,6,6-Trimethylbicyclo[3.1.1]-hept-3-yl | |
| 69 | H | Phenyl | IR: 2960, 2928, 2863, 1602, 1503, 1362, 1312, 827, 746, 691 |
| 70 | H | 2-Methylphenyl | |
| 71 | | 3-Methylphenyl | |
| 72 | H | 4-Methylphenyl | |
| 73 | H | 2,4-Dimethylphenyl | |
| 74 | H | 4-Isopropylphenyl | |
| 75 | H | 4-tert.-Butylphenyl | IR: 2961, 2928, 2864, 1615, 1519, 1460, 1445, 1363, 1269, 1193, 819 |
| 76 | H | 2-Methoxyphenyl | IR: 2960, 2931, 2863, 1602, 1519, 1512, 1456, 1247, 1222, 734 |
| 77 | H | 4-Methoxyphenyl | IR: 2952, 2925, 2863, 1512, 1461, 1458, 1255, 1248, 1031, 823 |
| 78 | H | 3,4-Dimethoxyphenyl | |
| 79 | H | 4-tert.-Butyoxyphenyl | |
| 80 | H | 2-Trifluoromethylphenyl | |
| 81 | H | 3-Trifluoromethylphenyl | |
| 82 | H | 4-Trifluoromethylphenyl | |
| 83 | H | 4-Trifluoromethoxyphenyl | |
| 84 | H | 2-Fluorophenyl | IR: 2961, 2930, 2864, 1620, 1521, 1512, 1449, 1249, 1185, 820, 740 |
| 85 | H | 3-Fluorophenyl | |
| 86 | H | 4-Fluorophenyl | IR: 2960, 2931, 2865, 1508, 1540, 1220, 1211, 823, 711, 571 |
| 87 | H | 2,4-Difluorophenyl | |
| 88 | H | 2-Chlorophenyl | |
| 89 | H | 2-Chloro-4-fluorphenyl | |
| 90 | H | 3-Chlorophenyl | |
| 91 | H | 4-Chlorophenyl | IR: 2960, 2929, 2863, 1600, 1498, 1448, 1362, 1314, 826, 814 |
| 92 | H | 2,4-Dichlorophenyl | IR: 2960, 2929, 2864, 1592, 1505, 1461, 1449, 1362, 1321, 827 |
| 93 | H | 2,6-Dichlorophenyl | |
| 94 | H | 3,5-Dichlorophenyl | |
| 95 | H | 2-Cyanophenyl | |
| 96 | H | 3-Cyanophenyl | |
| 97 | H | 4-Cyanophenyl | |
| 98 | H | 2-Hydroxyphenyl | |
| 99 | H | 3-Hydroxyphenyl | |
| 100 | H | 4-Hydroxyphenyl | |
| 101 | H | 2-Nitrophenyl | |
| 102 | H | 3-Nitrophenyl | |

-continued

| No. | R¹ | R² | Physical data |
|---|---|---|---|
| 103 | H | 4-Nitrophenyl | |
| 104 | H | Benzyl | IR: 2961, 2927, 2862, 1461, 1452, 1362, 827, 736, 698, 572 |
| 105 | H | 2-Methylbenzyl | |
| 106 | H | 4-Methylbenzyl | |
| 107 | H | 2,4-Dimethylbenzyl | |
| 108 | H | 4-Isopropylbenzyl | |
| 109 | H | 4-tert.-Butylbenzyl | IR: 2961, 2925, 2863, 1509, 1460, 1448, 1362, 825, 571 |
| 110 | H | 2-Methoxybenzyl | |
| 111 | H | 3-Methoxybenzyl | |
| 112 | H | 4-Methoxylbenzyl | |
| 113 | H | 3,4-Dimethoxybenzyl | |
| 114 | H | 4-tert.-Butoxybenzyl | |
| 115 | H | 2-Trifluoromethylbenzyl | |
| 116 | H | 3-Trifluoromethylbenzyl | |
| 117 | H | 4-Trifluoromethylbenzyl | |
| 118 | H | 4-Trifluoromethoxybenzyl | |
| 119 | H | 2-Fluorobenzyl | IR: 2961, 2927, 28 64, 1508, 1490, 1456, 1363, 1229, 828, 756 |
| 120 | H | 3-Fluorobenzyl | |
| 121 | H | 4-Fluorobenzyl | IR: 2960, 2927, 2864, 1509, 1462, 1449, 1362, 1221, 827, 572 |
| 122 | H | 2,4-Difluorobenzyl | |
| 123 | H | 2-Chloro-4-fluorobenzyl | |
| 124 | H | 2-Chlorobenzyl | |
| 125 | H | 3-Chlorobenzyl | |
| 126 | H | 4-Chlorobenzyl | |
| 127 | H | 2,4-Dichlorobenzyl | Hydrochloride: IR: 2955, 2863, 2766, 2721, 2574, 1478, 1469, 825 |
| 128 | H | 2,6-Dichlorobenzyl | |
| 129 | H | 3,5-Dichlorobenzyl | |
| 130 | H | 2-Cyanobenzyl | |
| 131 | H | 4-Cyanobenzyl | |
| 132 | H | 2-Hydroxybenzyl | |
| 133 | H | 3-Hydroxybenzyl | |
| 134 | H | 4-Hydroxybenzyl | |
| 135 | H | 2-Nitrobenzyl | |
| 136. | H | 3-Nitrobenzyl | |
| 137 | H | 4-Nitrobenzyl | |
| 138 | H | 2,4-Dinitrobenzyl | |
| 139 | H | 2-Phenylethyl | |
| 140 | H | 2-(4-Methylphenyl)ethyl | |
| 141 | H | 2-(4-tert.-Butylphenyl)ethyl | |
| 142 | H | 2-(2-Methoxyphenyl)ethyl | |
| 143 | H | 2-(4-Methoxyphenyl)ethyl | |
| 144 | H | 2-(3,4-Dimethoxyphenyl)ethyl | |
| 145 | H | 2-(4-tert.-Butoxyphenyl)ethyl | |
| 146 | H | 2-(4-Trifluoromethoxyphenyl)ethyl | |
| 147 | H | 2-(3-Trifluoromethylphenyl)ethyl | |
| 148 | H | 2-(2-Fluorophenyl)ethyl | |
| 149 | H | 2-(4-Fluorophenyl)ethyl | |
| 150 | H | 2-(2-Chlorophenyl)ethyl | |
| 151 | H | 2-(4-Chlorophenyl)ethyl | |
| 152 | H | 2-(2,4-Dichlorophenyl)ethyl | |
| 153 | H | 2-(2-Chloro-4-fluorophenyl)ethyl | |
| 154 | H | 2-(4-Cyanophenyl)ethyl | |
| 155 | H | 2-(4-Hydroxyphenyl)ethyl | |
| 156 | H | 2-(4-Nitrophenyl)ethyl | |
| 157 | H | 3-Phenylpropyl | |
| 158 | H | 3-(4-Methylphenyl)propyl | |
| 159 | H | 3-(4-tert.-Butylphenyl)propyl | |
| 160 | H | 3-(2-Methoxyphenyl)propyl | |
| 161 | H | 3-(4-Methoxyphenyl)propyl | |
| 162 | H | 3-(3,4-Dimethoxyphenyl)propyl | |
| 163 | H | 3-(4-tert.-Butoxyphenyl)phenyl | |
| 164 | H | 3-(3-Trifluoromethylphenyl)propyl | |
| 165 | H | 3-(4-Trifluoromethoxyphenyl)propyl | |
| 166 | H | 3-(2-Fluorophenyl)propyl | |
| 167 | H | 3-(4-Fluorophenyl)propyl | |
| 168 | H | 3-(2-Chlorophenyl)propyl | |
| 169 | H | 3-(4-Chlorophenyl)propyl | |
| 170 | H | 3-(2,4-Dichlorophenyl)propyl | |
| 171 | H | 3-(2-Chloro-4-fluorophenyl)propyl | |
| 172 | H | 3-(4-Cyanophenyl)propyl | |
| 173 | H | 3-(4-Hydroxyphenyl)propyl | |
| 174 | H | 3-(4-Nitrophenyl)propyl | |
| 175 | Methyl | 1-Pentyl | |
| 176 | Methyl | 2-Methyl-1-butyl | |
| 177 | Methyl | 2-Methyl-1-pentyl | |
| 178 | Methyl | 2-Ethyl-1-butyl | |

-continued

| No. | R¹ | R² | Physical data |
|---|---|---|---|
| 179 | Methyl | 2,2-Dimethyl-1-propyl | |
| 180 | Methyl | 3,3-Dimethyl-1-butyl | oil (cis/trans = 1:3) |
| 181 | Methyl | 3-Methyl-1-butyl | |
| 182 | Methyl | 1-Hexyl | |
| 183 | Methyl | 2-Methyl-1-hexyl | |
| 184 | Methyl | 2-Ethyl-1-hexyl | |
| 185 | Methyl | 2,4,4-Trimethyl-1-pentyl | |
| 186 | Methyl | 1-Heptyl | |
| 187 | Methyl | 1-Octyl | |
| 188 | Methyl | 1-Nonyl | |
| 189 | Methyl | 1-Decyl | |
| 190 | Methyl | 1-Undecyl | |
| 191 | Methyl | 1-Dodecyl | |
| 192 | Methyl | 2-Propen-1-yl | |
| 193 | Methyl | 2-Buten-1-yl | |
| 194 | Methyl | 2-Penten-1-yl | |
| 195 | Methyl | 2-Hexen-1-yl | |
| 196 | Methyl | 3-Methyl-2-buten-1-yl | |
| 197 | Methyl | 2,3-Dimethyl-2-buten-1-yl | |
| 198 | Methyl | 2-Hydroxyethyl | |
| 199 | Methyl | 6-Hydroxy-1-hexyl | |
| 200 | Methyl | 3-Chloro-1-butyl | |
| 201 | Methyl | 4-Chloro-1-butyl | |
| 202 | Methyl | 3-Chloro-2-methyl-1-propyl | |
| 203 | Methyl | Cyclopropyl | |
| 204 | Methyl | Cyclobutyl | |
| 205 | Methyl | Cyclopentyl | |
| 206 | Methyl | Cyclohexyl | |
| 207 | Methyl | Cycloheptyl | |
| 208 | Methyl | Cyclooctyl | |
| 209 | Methyl | Cyclodecyl | |
| 210 | Methyl | Cyclododecyl | |
| 211 | Methyl | 1-Methylcyclopropyl | |
| 212 | Methyl | 1-Methylcyclopentyl | |
| 213 | Methyl | 1-Methylcyclohexyl | |
| 214 | Methyl | 2-Methycyclohexyl | |
| 215 | Methyl | 3-Methylcyclohexyl | |
| 216 | Methyl | 4-Methylcyclohexyl | |
| 217 | Methyl | 2,2-Dimethylcyclohexyl | |
| 218 | Methyl | 3,3-Dimethylcyclohexyl | |
| 219 | Methyl | 4,4-Dimethylcyclohexyl | |
| 220 | Methyl | 2,6-Dimethylcyclohexyl | |
| 221 | Methyl | 3,3,5-Trimethylcyclohexyl | |
| 222 | Methyl | 3,3,5,5-Tetramethylcyclohexyl | |
| 223 | Methyl | 4-Ethylcyclohexyl | |
| 224 | Methyl | 4-Propylcyclohexyl | |
| 225 | Methyl | 4-Isopropylcyclohexyl | |
| 226 | Methyl | 4-tert.-Butylcyclohexyl | |
| 227 | Methyl | cis-4-tert.-Butylcyclohexyl | |
| 228 | Methyl | trans-4-tert.-Butylcyclohexyl | |
| 229 | Methyl | 4-tert.-Amylcyclohexyl | |
| 230 | Methyl | Bicyclo[2.2.1]-hept-2-yl | |
| 231 | Methyl | 1,7,7-Trimethyl-bicyclo[2.2.1]-hept-2-yl | |
| 232 | Methyl | Bicyclo[4.4.0]dec-2-yl | |
| 233 | Methyl | Bicyclo[4.4.0]dec-3-yl | |
| 234 | Methyl | 2,6,6-Trimethylbicyclo[3.1.1]-hept-3-yl | |
| 235 | Methyl | Phenyl | |
| 236 | Methyl | 2-Methylphenyl | |
| 237 | Methyl | 3-Methylphenyl | |
| 238 | Methyl | 4-Methylphenyl | |
| 239 | Methyl | 2,4-Dimethylphenyl | |
| 240 | Methyl | 4-Isopropylphenyl | |
| 241 | Methyl | 4-tert.-Butylphenyl | |
| 242 | Methyl | 2-Methoxyphenyl | |
| 243 | Methyl | 4-Methoxyphenyl | |
| 244 | Methyl | 3,4-Dimethoxyphenyl | |
| 245 | Methyl | 4-tert.-Butoxyphenyl | |
| 246 | Methyl | 2-Trifluoromethylphenyl | |
| 247 | Methyl | 3-Trifluoromethylphenyl | |
| 248 | Methyl | 4-Trifluoromethylphenyl | |
| 249 | Methyl | 4-Trifluoromethylphenyl | |
| 250 | Methyl | 2-Fluorophenyl | |
| 251 | Methyl | 3-Fluorophenyl | |
| 252 | Methyl | 4-Fluorophenyl | |
| 253 | Methyl | 2,4-Difluorophenyl | |
| 254 | Methyl | 2-Chlorophenyl | |
| 255 | Methyl | 2-Chloro-4-fluorphenyl | |
| 256 | Methyl | 3-Chlorophenyl | |
| 257 | Methyl | 4-Chlorophenyl | |
| 258 | Methyl | 2,4-Dichlorophenyl | |
| 259 | Methyl | 2,6-Dichlorophenyl | |

-continued

| No. | R¹ | R² | Physical data |
|---|---|---|---|
| 260 | Methyl | 3,5-Dichlorophenyl | |
| 261 | Methyl | 2-Cyanophenyl | |
| 262 | Methyl | 3-Cyanophenyl | |
| 263 | Methyl | 4-Cyanophenyl | |
| 264 | Methyl | 2-Hydroxyphenyl | |
| 265 | Methyl | 3-Hydroxyphenyl | |
| 266 | Methyl | 4-Hydroxyphenyl | |
| 267 | Methyl | 2-Nitrophenyl | |
| 268 | Methyl | 3-Nitrophenyl | |
| 269 | Methyl | 4-Nitrophenyl | |
| 270 | Methyl | Benzyl | |
| 271 | Methyl | 2-Methylbenzyl | |
| 272 | Methyl | 4-Methylbenzyl | |
| 273 | Methyl | 2,4-Dimethylbenzyl | |
| 274 | Methyl | 4-Isopropylbenzyl | |
| 275 | Methyl | 4-tert.-Butylbenzyl | |
| 276 | Methyl | 2-Methoxybenzyl | |
| 277 | Methyl | 3-Methoxybenzyl | |
| 278 | Methyl | 4-Methoxybenzyl | |
| 279 | Methyl | 3,4-Dimethoxybenzyl | |
| 280 | Methyl | 4-tert.-Butoxybenzyl | |
| 281 | Methyl | 2-Trifluoromethylbenzyl | |
| 282 | Methyl | 3-Trifluoromethylbenzyl | |
| 283 | Methyl | 4-Trifluoromethylbenzyl | |
| 284 | Methyl | 4-Trifluoromethoxybenzyl | |
| 285 | Methyl | 2-Fluorobenzyl | |
| 286 | Methyl | 3-Fluorobenzyl | |
| 287 | Methyl | 4-Fluorobenzyl | |
| 288 | Methyl | 2,4-Difluorobenzyl | |
| 289 | Methyl | 2-Chloro-4-fluorobenzyl | |
| 290 | Methyl | 2-Chlorobenzyl | |
| 291 | Methyl | 3-Chlorobenzyl | |
| 292 | Methyl | 4-Chlorobenzyl | |
| 293 | Methyl | 2,4-Dichlorobenzyl | |
| 294 | Methyl | 2,6-Dichlorobenzyl | |
| 295 | Methyl | 3,5-Dichlorobenzyl | |
| 296 | Methyl | 2-Cyanobenzyl | |
| 297 | Methyl | 4-Cyanobenzyl | |
| 298 | Methyl | 2-Hydroxybenzyl | |
| 299 | Methyl | 3-Hydroxybenzyl | |
| 300 | Methyl | 4-Hydroxybenzyl | |
| 301 | Methyl | 2-Nitrobenzyl | |
| 302 | Methyl | 3-Nitrobenzyl | |
| 303 | Methyl | 4-Nitrobenzyl | |
| 304 | Methyl | 2,4-Dinitrobenzyl | |
| 305 | Methyl | 2-Phenylethyl | |
| 306 | Methyl | 2-(4-Methylphenyl)ethyl | |
| 307 | Methyl | 2-(4-tert.-Butylphenyl)ethyl | |
| 308 | Methyl | 2-(2-Methoxyphenyl)ethyl | |
| 309 | Methyl | 2-(4-Methoxyphenyl)ethyl | |
| 310 | Methyl | 2-(3,4-Dimethoxyphenyl)ethyl | |
| 311 | Methyl | 2-(4-tert.-Butyoxyphenyl)ethyl | |
| 312 | Methyl | 2-(4-Trifluoromethoxyphenyl)ethyl | |
| 313 | Methyl | 2-(3-Trifluoromethylphenyl)ethyl | |
| 314 | Methyl | 2-(2-Fluorophenyl)ethyl | |
| 315 | Methyl | 2-(4-Fluorphenyl)ethyl | |
| 316 | Methyl | 2-(2-Chlorophenyl)ethyl | |
| 317 | Methyl | 2-(4-Chlorophenyl)ethyl | |
| 318 | Methyl | 2-(2,4-Dichlorophenyl)ethyl | |
| 319 | Methyl | 2-(2-Chloro-4-fluorophenyl)ethyl | |
| 320 | Methyl | 2-(4-Cyanophenyl)ethyl | |
| 321 | Methyl | 2-(4-Hydroxyphenyl)ethyl | |
| 322 | Methyl | 2-(4-Nitrophenyl)ethyl | |
| 323 | Methyl | 3-Phenylpropyl | |
| 324 | Methyl | 3-(4-Methylphenyl)propyl | |
| 325 | Methyl | 3-(4-tert.-Butylphenyl)propyl | |
| 326 | Methyl | 3-(2-Methoxyphenyl)propyl | |
| 327 | Methyl | 3-(4-Methoxyphenyl)propyl | |
| 328 | Methyl | 3-(3,4-Dimethoxyphenyl)propyl | |
| 329 | Methyl | 3-(4-tert.-Butoxyphenyl)propyl | |
| 330 | Methyl | 3-(3-Trifluoromethylphenyl)propyl | |
| 331 | Methyl | 3-(4-Trifluoromethoxyphenyl)propyl | |
| 332 | Methyl | 3-(2-Fluorphenyl)propyl | |
| 333 | Methyl | 3-(4-Fluorphenyl)propyl | |
| 334 | Methyl | 3-(2-chlorphenyl)propyl | |
| 335 | Methyl | 3-(4-Chlorophenyl)propyl | |
| 336 | Methyl | 3-(2,4-Dichlorophenyl)propyl | |
| 337 | Methyl | 3-(2-Chloro-4-fluorophenyl)propyl | |
| 338 | Methyl | 3-(4-Cyanophenyl)propyl | |
| 339 | Methyl | 3-(4-Hydroxyphenyl)propyl | |
| 340 | Methyl | 3-(4-Nitrophenyl)propyl | |

-continued

| No. | R¹ | R² | Physical data |
|---|---|---|---|
| 341 | Ethyl | 1-Pentyl | |
| 342 | Ethyl | 2-Methyl-1-butyl | |
| 343 | Ethyl | 2-Methyl-1-pentyl | |
| 344 | Ethyl | 2-Ethyl-1-butyl | |
| 345 | Ethyl | 2,2-Dimethyl-1-propyl | |
| 346 | Ethyl | 3,3-Dimethyl-1-butyl | |
| 347 | Ethyl | 3-Methyl-1-butyl | |
| 348 | Ethyl | 1-Hexyl | |
| 349 | Ethyl | 2-Methyl-1-hexyl | |
| 350 | Ethyl | 2-Ethyl-1-hexyl | |
| 351 | Ethyl | 2,4,4-Trimethy-1-pentyl | |
| 352 | Ethyl | 1-Heptyl | |
| 353 | Ethyl | 1-Octyl | |
| 354 | Ethyl | 1-Nonyl | |
| 355 | Ethyl | 1-Decyl | |
| 356 | Ethyl | 1-Undecyl | |
| 357 | Ethyl | 1-Dodecyl | |
| 358 | Ethyl | 2-Propen-1-yl | |
| 359 | Ethyl | 2-Buten-1-yl | |
| 360 | Ethyl | 2-Penten-1-yl | |
| 361 | Ethyl | 2-Hexen-1-yl | |
| 362 | Ethyl | 3-Methyl-2-buten-1-yl | |
| 363 | Ethyl | 2,3-Dimethyl-2-buten-1-yl | |
| 364 | Ethyl | 2-Hydroxyethyl | |
| 365 | Ethyl | 6-Hydroxy-1-hexyl | |
| 366 | Ethyl | 3-Chloro-1-butyl | |
| 367 | Ethyl | 4-Chloro-1-butyl | |
| 368 | Ethyl | 3-Chloro-2-methyl-1-propyl | |
| 369 | Ethyl | Cyclopropyl | |
| 370 | Ethyl | Cyclobutyl | |
| 371 | Ethyl | Cyclopentyl | |
| 372 | Ethyl | Cyclohexyl | |
| 373 | Ethyl | Cycloheptyl | |
| 374 | Ethyl | Cyclooctyl | |
| 375 | Ethyl | Cyclodecyl | |
| 376 | Ethyl | Cyclododecyl | |
| 377 | Ethyl | 1-Methylcyclopropyl | |
| 378 | Ethyl | 1-Methylcyclopentyl | |
| 379 | Ethyl | 1-Methylcyclohexyl | |
| 380 | Ethyl | 2-Methylcyclohexyl | |
| 381 | Ethyl | 3-Methylcyclohexyl | |
| 382 | Ethyl | 4-Methylcyclohexyl | |
| 383 | Ethyl | 2,2-Dimethylcyclohexyl | |
| 384 | Ethyl | 3,3-Dimethylcyclohexyl | |
| 385 | Ethyl | 4,4-Dimethylcyclohexyl | |
| 386 | Ethyl | 2,6-Dimethylcyclohexyl | |
| 387 | Ethyl | 3,3,5-Trimethylcyclohexyl | |
| 388 | Ethyl | 3,3,5,5-Tetramethylcyclohexyl | |
| 389 | Ethyl | 4-Ethylcyclohexyl | |
| 390 | Ethyl | 4-Propylcyclohexyl | |
| 391 | Ethyl | 4-Isopropylcyclohexyl | |
| 392 | Ethyl | 4-tert.-Butylcyclohexyl | |
| 393 | Ethyl | cis-4-tert.-Butylcyclohexyl | |
| 394 | Ethyl | trans-4-tert.-Butylcyclohexyl | Hydrochloride mp. 185–186° C. |
| 395 | Ethyl | 4-tert.-Amylcyclohexyl | |
| 396 | Ethyl | Bicyclo[2.2.1]-hept-2-yl | |
| 397 | Ethyl | 1,7,7-Trimethyl- bicyclo[2.2.1]-hept-2-yl | |
| 398 | Ethyl | Bicyclo[4.4.0]dec-2-yl | |
| 399 | Ethyl | Bicyclo[4.4.0]dec-3-yl | |
| 400 | Ethyl | 2,6,6-Trimethylbicyclo[3.1.1]-hept-3-yl | |
| 401 | Ethyl | Phenyl | |
| 402 | Ethyl | 2-Methylphenyl | |
| 403 | Ethyl | 3-Methylphenyl | |
| 404 | Ethyl | 4-Methylphenyl | |
| 405 | Ethyl | 2,4-Dimethylphenyl | |
| 406 | Ethyl | 4-Isopropylphenyl | |
| 407 | Ethyl | 4-tert.-Butylphenyl | |
| 408 | Ethyl | 2-Methoxyphenyl | |
| 409 | Ethyl | 4-Methoxyphenyl | |
| 410 | Ethyl | 3,4-Dimethoxyphenyl | |
| 411 | Ethyl | 4-tert.-Butoxyphenyl | |
| 412 | Ethyl | 2-Trifluoromethylphenyl | |
| 413 | Ethyl | 3-Trifluoromethylphenyl | |
| 414 | Ethyl | 4-Trifluoromethylphenyl | |
| 415 | Ethyl | 4-Trifluoromethoxyphenyl | |
| 416 | Ethyl | 2-Fluorophenyl | |
| 417 | Ethyl | 3-Fluorophenyl | |
| 418 | Ethyl | 4-Fluorophenyl | |
| 419 | Ethyl | 2,4-Difluorophenyl | |
| 420 | Ethyl | 2-Chlorophenyl | |
| 421 | Ethyl | 2-Chloro-4-fluorophenyl | |

-continued

| No. | R¹ | R² | Physical data |
|---|---|---|---|
| 422 | Ethyl | 3-Chlorophenyl | |
| 423 | Ethyl | 4-Chlorophenyl | |
| 424 | Ethyl | 2,4-Dichlorophenyl | |
| 425 | Ethyl | 2,6-Dichlorophenyl | |
| 426 | Ethyl | 3,5-Dichlorophenyl | |
| 427 | Ethyl | 2-Cyanophenyl | |
| 428 | Ethyl | 3-Cyanophenyl | |
| 429 | Ethyl | 4-Cyanophenyl | |
| 430 | Ethyl | 2-Hydroxyphenyl | |
| 431 | Ethyl | 3-Hydroxyphenyl | |
| 432 | Ethyl | 4-Hydroxyphenyl | |
| 433 | Ethyl | 2-Nitrophenyl | |
| 434 | Ethyl | 3-Nitrophenyl | |
| 435 | Ethyl | 4-Nitrophenyl | |
| 436 | Ethyl | Benzyl | |
| 437 | Ethyl | 2-Methylbenzyl | |
| 438 | Ethyl | 4-Methylbenzyl | |
| 439 | Ethyl | 2,4-Dimethylbenzyl | |
| 440 | Ethyl | 4-Isopropylbenzyl | |
| 441 | Ethyl | 4-tert.-Butylbenzyl | |
| 442 | Ethyl | 2-Methoxybenzyl | |
| 443 | Ethyl | 3-Methoxybenzyl | |
| 444 | Ethyl | 4-Methoxybenzyl | |
| 445 | Ethyl | 3,4-Dimethoxybenzyl | |
| 446 | Ethyl | 4-tert.-Butoxybenzyl | |
| 447 | Ethyl | 2-Trifluoromethylbenzyl | |
| 448 | Ethyl | 3-Trifluoromethylbenzyl | |
| 449 | Ethyl | 4-Trifluoromethylbenzyl | |
| 450 | Ethyl | 4-Trifluoromethoxybenzyl | |
| 451 | Ethyl | 2-Fluorobenzyl | |
| 452 | Ethyl | 3-Fluorobenzyl | |
| 453 | Ethyl | 4-Fluorobenzyl | |
| 454 | Ethyl | 2,4-Difluorobenzyl | |
| 455 | Ethyl | 2-Chloro-4-fluorobenzyl | |
| 456 | Ethyl | 2-Chlorobenzyl | |
| 457 | Ethyl | 3-Chlorobenzyl | |
| 458 | Ethyl | 4-Chlorobenzyl | |
| 459 | Ethyl | 2,4-Dichlorobenzyl | |
| 460 | Ethyl | 2,6-Dichlorobenzyl | |
| 461 | Ethyl | 3,5-Dichlorobenzyl | |
| 462 | Ethyl | 2-Cyanobenzyl | |
| 463 | Ethyl | 4-Cyanobenzyl | |
| 464 | Ethyl | 2-Hydroxybenzyl | |
| 465 | Ethyl | 3-Hydroxybenzyl | |
| 466 | Ethyl | 4-Hydroxybenzyl | |
| 467 | Ethyl | 2-Nitrobenzyl | |
| 468 | Ethyl | 3-Nitrobenzyl | |
| 469 | Ethyl | 4-Nitrobenzyl | |
| 470 | Ethyl | 2,4-Dinitrobenzyl | |
| 471 | Ethyl | 2-Phenylethyl | |
| 472 | Ethyl | 2-(4-Methylphenyl)ethyl | |
| 473 | Ethyl | 2-(4-tert.-Butylphenyl)ethyl | |
| 474 | Ethyl | 2-(2-Methoxyphenyl)ethyl | |
| 475 | Ethyl | 2-(4-Methoxyphenyl)ethyl | |
| 476 | Ethyl | 2-(3,4-Dimethoxyphenyl)ethyl | |
| 477 | Ethyl | 2-(4-tert.-Butoxyphenyl)ethyl | |
| 478 | Ethyl | 2-(4-Trifluoromethoxyphenyl)ethyl | |
| 479 | Ethyl | 2-(3-Trifluoromethylphenyl)ethyl | |
| 480 | Ethyl | 2-(2-Fluorophenyl)ethyl | |
| 481 | Ethyl | 2-(4-Fluorophenyl)ethyl | |
| 482 | Ethyl | 2-(2-Chlorophenyl)ethyl | |
| 483 | Ethyl | 2-(4-Chlorophenyl)ethyl | |
| 484 | Ethyl | 2-(2,4-Dichlorophenyl)ethyl | |
| 485 | Ethyl | 2-(2-Chloro-4-fluorophenyl)ethyl | |
| 486 | Ethyl | 2-(4-Cyanophenyl)ethyl | |
| 487 | Ethyl | 2-(4-Hydroxyphenyl)ethyl | |
| 488 | Ethyl | 2-(4-Nitrophenyl)ethyl | |
| 489 | Ethyl | 3-Phenylpropyl | |
| 490 | Ethyl | 3-(4-Methylphenyl)propyl | |
| 491 | Ethyl | 3-(4-tert.-Butylphenyl)propyl | |
| 492 | Ethyl | 3-(2-Methoxyphenyl)propyl | |
| 493 | Ethyl | 3-(4-Methoxyphenyl)propyl | |
| 494 | Ethyl | 3-(3,4-Dimethoxyphenyl)propyl | |
| 495 | Ethyl | 3-(4-tert.-Butoxyphenyl)propyl | |
| 496 | Ethyl | 3-(3-Trifluoromethylphenyl)propyl | |
| 497 | Ethyl | 3-(4-Trifluoromethoxyphenyl)propyl | |
| 498 | Ethyl | 3-(2-Fluorophenyl)propyl | |
| 499 | Ethyl | 3-(4-Fluorophenyl)propyl | |
| 500 | Ethyl | 3-(2-Chlorophenyl)propyl | |
| 501 | Ethyl | 3-(4-Chlorophenyl)propyl | |
| 502 | Ethyl | 3-(2,4-Dichlorophenyl)propyl | |

-continued

| No. | R¹ | R² | Physical data |
|---|---|---|---|
| 503 | Ethyl | 3-(2-Chloro-4-fluorophenyl)propyl | |
| 504 | Ethyl | 3-(4-Cyanophenyl)propyl | |
| 505 | Ethyl | 3-(4-Hydroxyphenyl)propyl | |
| 506 | Ethyl | 3-(4-Nitrophenyl)propyl | |
| 507 | 1-Propyl | 1-Pentyl | |
| 508 | 1-Propyl | 2-Methyl-1-butyl | |
| 509 | 1-Propyl | 2-Methyl-1-pentyl | |
| 510 | 1-Propyl | 2-Ethyl-1-butyl | |
| 511 | 1-Propyl | 2,2-Dimethyl-1-propyl | |
| 512 | 1-Propyl | 3,3-Dimethyl-1-butyl | |
| 513 | 1-Propyl | 3-Methyl-1-butyl | |
| 514 | 1-Propyl | 1-Hexyl | |
| 515 | 1-Propyl | 2-Methyl-1-hexyl | |
| 516 | 1-Propyl | 2-Ethyl-1-hexyl | |
| 517 | 1-Propyl | 2,4,4-Trimethyl-1-pentyl | |
| 518 | 1-Propyl | 1-Heptyl | |
| 519 | 1-Propyl | 1-Octyl | |
| 520 | 1-Propyl | 1-Nonyl | |
| 521 | 1-Propyl | 1-Decyl | |
| 522 | 1-Propyl | 1-Undecyl | |
| 523 | 1-Propyl | 1-Dodecyl | |
| 524 | 1-Propyl | 2-Propen-1-yl | |
| 525 | 1-Propyl | 2-Buten-1-yl | |
| 526 | 1-Propyl | 2-Penten-1-yl | |
| 527 | 1-Propyl | 2-Hexen-1-yl | |
| 528 | 1-Propyl | 3-Methyl-2-buten-1-yl | |
| 529 | 1-Propyl | 2,3-Dimethyl-2-buten-1-yl | |
| 530 | 1-Propyl | 2-Hydroxyethyl | |
| 531 | 1-Propyl | 6-Hydroxy-1-hexyl | |
| 532 | 1-Propyl | 3-Chloro-1-butyl | |
| 533 | 1-Propyl | 4-Chloro-1-butyl | |
| 534 | 1-Propyl | 3-Chloro-2-methyl-1-propyl | |
| 535 | 1-Propyl | Cyclopropyl | |
| 536 | 1-Propyl | Cyclobutyl | |
| 537 | 1-Propyl | Cyclopentyl | |
| 538 | 1-Propyl | Cyclohexyl | |
| 539 | 1-Propyl | Cycloheptyl | |
| 540 | 1-Propyl | Cyclooctyl | |
| 541 | 1-Propyl | Cyclododecyl | |
| 542 | 1-Propyl | Cyclododecyl | |
| 543 | 1-Propyl | 1-Methylcyclopropyl | |
| 544 | 1-Propyl | 1-Methylcyclopentyl | |
| 545 | 1-Propyl | 1-Methylcyclohexyl | |
| 546 | 1-Propyl | 2-Methylcyclohexyl | |
| 547 | 1-Propyl | 3-Methylcyclohexyl | |
| 548 | 1-Propyl | 4-Methylcyclohexyl | |
| 549 | 1-Propyl | 2,2-Dimethylcyclohexyl | |
| 550 | 1-Propyl | 3,3-Dimethylcyclohexyl | |
| 551 | 1-Propyl | 4,4-Dimethylcyclohexyl | |
| 552 | 1-Propyl | 2,6-Dimethylcyclohexyl | |
| 553 | 1-Propyl | 3,3,5-Trimethylcyclohexyl | |
| 554 | 1-Propyl | 3,3,5,5-Tetramethylcyclohexyl | |
| 555 | 1-Propyl | 4-Ethylcyclohexyl | |
| 556 | 1-Propyl | 4-Propylcyclohexyl | |
| 557 | 1-Propyl | 4-Isopropylcyclohexyl | |
| 558 | 1-Propyl | 4-tert.-Butylcyclohexyl | |
| 559 | 1-Propyl | cis-4-tert.-Butylcyclohexyl | |
| 560 | 1-Propyl | trans-4-tert.-Butylcyclohexyl | bp 230–236° C./0.2 mbar |
| 561 | 1-Propyl | 4-tert.-Amylcyclohexyl | |
| 562 | 1-Propyl | Bicyclo[2.2.1]-hept-2-yl | |
| 563 | 1-Propyl | 1,7,7-Trimethyl-bicyclo[2.2.1]-hept-2-yl | |
| 564 | 1-Propyl | Bicyclo[4.4.0]dec-2-yl | |
| 565 | 1-Propyl | Bicyclo[4.4.0]dec-3-yl | |
| 566 | 1-Propyl | 2,6,6-Trimethylbicyclo[3.1.1]-hept-3-yl | |
| 567 | 1-Propyl | Phenyl | |
| 568 | 1-Propyl | 2-Methylphenyl | |
| 569 | 1-Propyl | 3-Methylphenyl | |
| 570 | 1-Propyl | 4-Methylphenyl | |
| 571 | 1-Propyl | 2,4-Dimethylphenyl | |
| 572 | 1-Propyl | 4-Isopropylphenyl | |
| 573 | 1-Propyl | 4-tert.-Butylphenyl | |
| 574 | 1-Propyl | 2-Methoxyphenyl | |
| 575 | 1-Propyl | 4-Methoxyphenyl | |
| 576 | 1-Propyl | 3,4-Dimethoxyphenyl | |
| 577 | 1-Propyl | 4-tert.-Butoxyphenyl | |
| 578 | 1-Propyl | 2-Trifluoromethylphenyl | |
| 579 | 1-Propyl | 3-Trifluoromethylphenyl | |
| 580 | 1-Propyl | 4-Trifluoromethylphenyl | |
| 581 | 1-Propyl | 4-Trifluoromethoxyphenyl | |
| 582 | 1-Propyl | 2-Fluorophenyl | |
| 583 | 1-Propyl | 3-Fluorophenyl | |

-continued

| No. | R¹ | R² | Physical data |
|---|---|---|---|
| 584 | 1-Propyl | 4-Fluorophenyl | |
| 585 | 1-Propyl | 2,4-Difluorophenyl | |
| 586 | 1-Propyl | 2-Chlorophenyl | |
| 587 | 1-Propyl | 2-Chloro-4-fluorophenyl | |
| 588 | 1-Propyl | 3-Chlorophenyl | |
| 589 | 1-Propyl | 4-Chlorophenyl | |
| 590 | 1-Propyl | 2,4-Dichlorophenyl | |
| 591 | 1-Propyl | 2,6-Dichlorophenyl | |
| 592 | 1-Propyl | 3,5-Dichlorophenyl | |
| 593 | 1-Propyl | 2-Cyanophenyl | |
| 594 | 1-Propyl | 3-Cyanophenyl | |
| 595 | 1-Propyl | 4-Cyanophenyl | |
| 596 | 1-Propyl | 2-Hydroxyphenyl | |
| 597 | 1-Propyl | 3-Hydroxyphenyl | |
| 598 | 1-Propyl | 4-Hydroxyphenyl | |
| 599 | 1-Propyl | 2-Nitrophenyl | |
| 600 | 1-Propyl | 3-Nitrophenyl | |
| 601 | 1-Propyl | 4-Nitrophenyl | |
| 602 | 1-Propyl | Benzyl | |
| 603 | 1-Propyl | 2-Methylbenzyl | |
| 604 | 1-Propyl | 4-Methylbenzyl | |
| 605 | 1-Propyl | 2,4-Dimethylbenzyl | |
| 606 | 1-Propyl | 4-Isopropylbenzyl | |
| 607 | 1-Propyl | 4-tert.-Butylbenzyl | |
| 608 | 1-Propyl | 2-Methoxybenzyl | |
| 609 | 1-Propyl | 3-Methoxybenzyl | |
| 610 | 1-Propyl | 4-Methoxybenzyl | |
| 611 | 1-Propyl | 3,4-Dimethoxybenzyl | |
| 612 | 1-Propyl | 4-tert.-Butoxybenzyl | |
| 613 | 1-Propyl | 2-Trifluoromethylbenzyl | |
| 614 | 1-Propyl | 3-Trifluoromethylbenzyl | |
| 615 | 1-Propyl | 4-Trifluoromethylbenzyl | |
| 616 | 1-Propyl | 4-Trifluoromethoxybenzyl | |
| 617 | 1-Propyl | 2-Fluorobenzyl | |
| 618 | 1-Propyl | 3-Fluorobenzyl | |
| 619 | 1-Propyl | 4-Fluorobenzyl | |
| 620 | 1-Propyl | 2,4-Difluorobenzyl | |
| 621 | 1-Propyl | 2-Chloro-4-fluorobenzyl | |
| 622 | 1-Propyl | 2-Chlorobenzyl | |
| 623 | 1-Propyl | 3-Chlorobenzyl | |
| 624 | 1-Propyl | 4-Chlorobenzyl | |
| 625 | 1-Propyl | 2,4-Dichlorobenzyl | |
| 626 | 1-Propyl | 2,6-Dichlorobenzyl | |
| 627 | 1-Propyl | 3,5-Dichlorobenzyl | |
| 628 | 1-Propyl | 2-Cyanobenzyl | |
| 629 | 1-Propyl | 4-Cyanobenzyl | |
| 630 | 1-Propyl | 2-Hydroxybenzyl | |
| 631 | 1-Propyl | 3-Hydroxybenzyl | |
| 632 | 1-Propyl | 4-Hydroxybenzyl | |
| 633 | 1-Propyl | 2-Nitrobenzyl | |
| 634 | 1-Propyl | 3-Nitrobenzyl | |
| 635 | 1-Propyl | 4-Nitrobenzyl | |
| 636 | 1-Propyl | 2,4-Dinitrobenzyl | |
| 637 | 1-Propyl | 2-Phenylethyl | |
| 638 | 1-Propyl | 2-(4-Methylphenyl)ethyl | |
| 639 | 1-Propyl | 2-(4-tert.-Butylphenyl)ethyl | |
| 640 | 1-Propyl | 2-(2-Methoxyphenyl)ethyl | |
| 641 | 1-Propyl | 2-(4-Methoxyphenyl)ethyl | |
| 642 | 1-Propyl | 2-(3,4-Dimethoxyphenyl)ethyl | |
| 643 | 1-Propyl | 2-(4-tert.-Butoxyphenyl)ethyl | |
| 644 | 1-Propyl | 2-(4-Trifluoromethoxyphenyl)ethyl | |
| 645 | 1-Propyl | 2-(3-Trifluoromethylphenyl)ethyl | |
| 646 | 1-Propyl | 2-(2-Fluorophenyl)ethyl | |
| 647 | 1-Propyl | 2-(4-Fluorophenyl)ethyl | |
| 648 | 1-Propyl | 2-(2-Chlorophenyl)ethyl | |
| 649 | 1-Propyl | 2-(4-chlorophenyl)ethyl | |
| 650 | 1-Propyl | 2-(2,4-Dichlorophenyl)ethyl | |
| 651 | 1-Propyl | 2-(2-Chloro-4-fluorophenyl)ethyl | |
| 652 | 1-Propyl | 2-(4-Cyanophenyl)ethyl | |
| 653 | 1-Propyl | 2-(4-Hydroxyphenyl)ethyl | |
| 654 | 1-Propyl | 2-(4-Nitrophenyl)ethyl | |
| 655 | 1-Propyl | 3-Phenylpropyl | |
| 656 | 1-Propyl | 3-(4-Methylphenyl)propyl | |
| 657 | 1-Propyl | 3-(4-tert.-Butylphenyl)propyl | |
| 658 | 1-Propyl | 3-(2-Methoxyphenyl)propyl | |
| 659 | 1-Propyl | 3-(4-Methoxyphenyl)propyl | |
| 660 | 1-Propyl | 3-(3,4-Dimethoxyphenyl)propyl | |
| 661 | 1-Propyl | 3-(4-tert.-Butoxyphenyl)propyl | |
| 662 | 1-Propyl | 3-(3-Trifluoromethylphenyl)propyl | |
| 663 | 1-Propyl | 3-(4-Trifluoromethoxyphenyl)propyl | |
| 664 | 1-Propyl | 3-(2-Fluorophenyl)propyl | |

-continued

| No. | R¹ | R² | Physical data |
|---|---|---|---|
| 665 | 1-Propyl | 3-(4-Fluorophenyl)propyl | |
| 666 | 1-Propyl | 3-(2-(Chlorophenyl)propyl | |
| 667 | 1-Propyl | 3-(4-Chlorophenyl)propyl | |
| 668 | 1-Propyl | 3-(2,4-Dichlorophenyl)propyl | |
| 669 | 1-Propyl | 3-(2-Chloro-4-fluorophenyl)propyl | |
| 670 | 1-Propyl | 3-(4-Cyanophenyl)propyl | |
| 671 | 1-Propyl | 3-(4-Hydroxyphenyl)propyl | |
| 672 | 1-Propyl | 3-(4-Nitrophenyl)propyl | |
| 673 | 2-Propen-1-yl | Methyl | |
| 674 | 2-Propen-1-yl | Ethyl | |
| 675 | 2-Propen-1-yl | 1-Propyl | |
| 676 | 2-Propen-1-yl | 2-Propyl | |
| 677 | 2-Propen-1-yl | 1-Butyl | |
| 678 | 2-Propen-1-yl | 2-Butyl | |
| 679 | 2-Propen-1-yl | tert.-Butyl | |
| 680 | 2-Propen-1-yl | 2-Methyl-1-propyl | |
| 681 | 2-Propen-1-yl | 1-Pentyl | |
| 682 | 2-Propen-1-yl | 2-Methyl-1-butyl | |
| 683 | 2-Propen-1-yl | 2-Methyl-1-pentyl | |
| 684 | 2-Propen-1-yl | 2-Ethyl-1-butyl | |
| 685 | 2-Propen-1-yl | 2,2-Dimethyl-1-propyl | |
| 686 | 2-Propen-1-yl | 3,3-Dimethyl-1-butyl | |
| 687 | 2-Propen-1-yl | 3-Methyl-1-butyl | |
| 688 | 2-Propen-1-yl | 1-Hexyl | |
| 689 | 2-Propen-1-yl | 2-Methyl-1-hexyl | |
| 690 | 2-Propen-1-yl | 2-Ethyl-1-hexyl | |
| 691 | 2-Propen-1-yl | 2,4,4-Trimethyl-1-pentyl | |
| 692 | 2-Propen-1-yl | 1-Heptyl | |
| 693 | 2-Propen-1-yl | 1-Octyl | |
| 694 | 2-Propen-1-yl | 1-Nonyl | |
| 695 | 2-Propen-2-yl | 1-Decyl | |
| 696 | 2-Propen-1-yl | 1-Undecyl | |
| 697 | 2-Propen-1-yl | 1-Dodecyl | |
| 698 | 2-Propen-1-yl | 2-Propen-1-yl | |
| 699 | 2-Propen-1-yl | 2-Buten-1-yl | |
| 700 | 2-Propen-1-yl | 2-Penten-1-yl | |
| 701 | 2-Propen-1-yl | 2-Hexen-1-yl | |
| 702 | 2-Propen-1-yl | 3-Methyl-2-buten-1-yl | |
| 703 | 2-Propen-1-yl | 2,3-Dimethyl-2-buten-1-yl | |
| 704 | 2-Propen-1-yl | 2-Hydroxyethyl | |
| 705 | 2-Propen-1-yl | 6-Hydroxy-1-hexyl | |
| 706 | 2-Propen-1-yl | 3-Chloro-1-butyl | |
| 707 | 2-Propen-1-yl | 4-Chloro-1-butyl | |
| 708 | 2-Propen-1-yl | 3-Chloro-2-methyl-1-propyl | |
| 709 | 2-Propen-1-yl | Cyclopropyl | |
| 710 | 2-Propen-1-yl | Cyclobutyl | |
| 711 | 2-Propen-1-yl | Cyclopentyl | |
| 712 | 2-Propen-1-yl | Cyclohexyl | |
| 713 | 2-Propen-1-yl | Cycloheptyl | |
| 714 | 2-Propen-1-yl | Cyclooctyl | |
| 715 | 2-Propen-1-yl | Cyclodecyl | |
| 716 | 2-Propen-1-yl | Cyclododecyl | |
| 717 | 2-Propen-1-yl | 1-Methylcyclopropyl | |
| 718 | 2-Propen-1-yl | 1-Methylcyclopentyl | |
| 719 | 2-Propen-1-yl | 1-Methylcyclohexyl | |
| 720 | 2-Propen-1-yl | 2-Methylcyclohexyl | |
| 721 | 2-Propen-1-yl | 3-Methylcyclohexyl | |
| 722 | 2-Propen-1-yl | 4-Methylcyclohexyl | |
| 723 | 2-Propen-1-yl | 2,2-Dimethylcyclohexyl | |
| 724 | 2-Propen-1-yl | 3,3-Dimethylcyclohexyl | |
| 725 | 2-Propen-1-yl | 4,4-Dimethylcyclohexyl | |
| 726 | 2-Propen-1-yl | 2,6-Dimethylcyclohexyl | |
| 727 | 2-Propen-1-yl | 3,3,5-Trimethylcyclohexyl | |
| 728 | 2-Propen-1-yl | 3,3,5,5-Tetramethylcyclohexyl | |
| 729 | 2-Propen-1-yl | 4-Ethylcyclohexyl | |
| 730 | 2-Propen-1-yl | 4-Propylcyclohexyl | |
| 731 | 2-Propen-1-yl | 4-Isopropylcyclohexyl | |
| 732 | 2-Propen-1-yl | 4-tert.-Butylcyclohexyl | |
| 733 | 2-Propen-1-yl | cis-4-tert.-Butylcyclohexyl | |
| 734 | 2-Propen-1-yl | trans-4-tert.-Butylcyclohexyl | resin (cis/trans = 2:3) |
| 735 | 2-Propen-1-yl | 4-tert.-Amylcyclohexyl | |
| 736 | 2-Propen-1-yl | Bicyclo[2.2.1]-hept-2-yl | |
| 737 | 2-Propen-1-yl | 1,7,7-Trimethyl-bicyclo[2.2.1]-hept-2-yl | |
| 738 | 2-Propen-1-yl | Bicyclo[4.4.0]dec-2-yl | |
| 739 | 2-Propen-1-yl | Bicyclo[4.4.0]dec-3-yl | |
| 740 | 2-Propen-1-yl | 2,6,6-Trimethylbicyclo[3.1.1]-hept-3-yl | |
| 741 | 2-Propen-1-yl | Phenyl | |
| 742 | 2-Propen-1-yl | 2-Methylphenyl | |
| 743 | 2-Propen-1-yl | 3-Methylphenyl | |
| 744 | 2-Propen-1-yl | 4-Methylphenyl | |
| 745 | 2-Propen-1-yl | 2,4-Dimethylphenyl | |

-continued

| No. | R¹ | R² | Physical data |
|---|---|---|---|
| 746 | 2-Propen-1-yl | 4-Isopropylphenyl | |
| 747 | 2-Propen-1-yl | 4-tert.-Butylphenyl | |
| 748 | 2-Propen-1-yl | 2-Methoxyphenyl | |
| 749 | 2-Propen-1-yl | 4-Methoxyphenyl | |
| 750 | 2-Propen-1-yl | 3,4-Dimethoxyphenyl | |
| 751 | 2-Propen-1-yl | 4-tert.-Butoxyphenyl | |
| 752 | 2-Propen-1-yl | 2-Trifluoromethylphenyl | |
| 753 | 2-Propen-1-yl | 3-Trifluoromethylphenyl | |
| 754 | 2-Propen-1-yl | 4-Trifluoromethylphenyl | |
| 755 | 2-Propen-1-yl | 4-Trifluoromethoxyphenyl | |
| 756 | 2-Propen-1-yl | 2-Fluorophenyl | |
| 757 | 2-Propen-1-yl | 3-Fluorophenyl | |
| 758 | 2-Propen-1-yl | 4-Fluorophenyl | |
| 759 | 2-Propen-1-yl | 2,4-Difluorophenyl | |
| 760 | 2-Propen-1-yl | 2-Chlorophenyl | |
| 761 | 2-Propen-1-yl | 2-Chloro-4-fluorophenyl | |
| 762 | 2-Propen-1-yl | 3-Chlorophenyl | |
| 763 | 2-Propen-1-yl | 4-Chlorophenyl | |
| 764 | 2-Propen-1-yl | 2,4-Dichlorophenyl | |
| 765 | 2-Propen-1-yl | 2,6-Dichlorophenyl | |
| 766 | 2-Propen-2-yl | 3,5-Dichlorophenyl | |
| 767 | 2-Propen-1-yl | 2-Cyanophenyl | |
| 768 | 2-Propen-1-yl | 3-Cyanophenyl | |
| 769 | 2-Propen-1-yl | 4-Cyanophenyl | |
| 770 | 2-Propen-1-yl | 2-Hydroxyphenyl | |
| 771 | 2-Propen-1-yl | 3-Hydroxyphenyl | |
| 772 | 2-Propen-1-yl | 4-Hydroxyphenyl | |
| 773 | 2-Propen-1-yl | 2-Nitrophenyl | |
| 774 | 2-Propen-1-yl | 3-Nitrophenyl | |
| 775 | 2-Propen-1-yl | 4-Nitrophenyl | |
| 776 | 2-Propen-1-yl | Benzyl | |
| 777 | 2-Propen-1-yl | 2-Methylbenzyl | |
| 778 | 2-Propen-1-yl | 4-Methylbenzyl | |
| 779 | 2-Propen-1-yl | 2,4-Dimethylbenzyl | |
| 780 | 2-Propen-1-yl | 4-Isopropylbenzyl | |
| 781 | 2-Propen-1-yl | 4-tert.-Butylbenzyl | |
| 782 | 2-Propen-1-yl | 2-Methoxybenzyl | |
| 783 | 2-Propen-1-yl | 3-Methoxybenzyl | |
| 784 | 2-Propen-1-yl | 4-Methoxybenzyl | |
| 785 | 2-Propen-1-yl | 3,4-Dimethoxybenzyl | |
| 786 | 2-Propen-1-yl | 4-tert.-Butoxybenzyl | |
| 787 | 2-Propen-1-yl | 2-Trifluoromethylbenzyl | |
| 788 | 2-Propen-1-yl | 3-Trifluoromethylbenzyl | |
| 789 | 2-Propen-1-yl | 4-Trifluoromethylbenzyl | |
| 790 | 2-Propen-1-yl | 4-Trifluoromethoxybenzyl | |
| 791 | 2-Propen-1-yl | 2-Fluorobenzyl | |
| 792 | 2-Propen-1-yl | 3-Fluorobenzyl | |
| 793 | 2-Propen-1-yl | 4-Fluorobenzyl | |
| 794 | 2-Propen-1-yl | 2,4-Difluorobenzyl | |
| 795 | 2-Propen-1-yl | 2-Chloro-4-fluorobenzyl | |
| 796 | 2-Propen-1-yl | 2-Chlorobenzyl | |
| 797 | 2-Propen-1-yl | 3-Chlorobenzyl | |
| 798 | 2-Propen-1-yl | 4-Chlorobenzyl | |
| 799 | 2-Propen-1-yl | 2,4-Dichlorobenzyl | |
| 800 | 2-Propen-1-yl | 2,6-Dichlorobenzyl | |
| 801 | 2-Propen-1-yl | 3,5-Dichlorobenzyl | |
| 802 | 2-Propen-1-yl | 2-Cyanobenzyl | |
| 803 | 2-Propen-1-yl | 4-Cyanobenzyl | |
| 804 | 2-Propen-1-yl | 2-Hydroxybenzyl | |
| 805 | 2-Propen-1-yl | 3-Hydroxybenzyl | |
| 806 | 2-Propen-1-yl | 4-Hydroxybenzyl | |
| 807 | 2-Propen-1-yl | 2-Nitrobenzyl | |
| 808 | 2-Propen-1-yl | 3-Nitrobenzyl | |
| 809 | 2-Propen-1-yl | 4-Nitrobenzyl | |
| 810 | 2-Propen-1-yl | 2,4-Dinitrobenzyl | |
| 811 | 2-Propen-1-yl | 2-Phenylethyl | |
| 812 | 2-Propen-1-yl | 2-(4-Methylphenyl)ethyl | |
| 813 | 2-Propen-1-yl | 2-(4-tert.-Butylphenyl)ethyl | |
| 814 | 2-Propen-1-yl | 2-(2-Methoxyphenyl)ethyl | |
| 815 | 2-Propen-1-yl | 2-(4-Methoxyphenyl)ethyl | |
| 816 | 2-Propen-1-yl | 2-(3,4-Dimethoxyphenyl)ethyl | |
| 817 | 2-Propen-1-yl | 2-(4-tert.-Butoxyphenyl)ethyl | |
| 818 | 2-Propen-1-yl | 2-(4-Trifluoromethoxyphenyl)ethyl | |
| 819 | 2-Propen-1-yl | 2-(3-Trifluoromethylphenyl)ethyl | |
| 820 | 2-Propen-1-yl | 2-(2-Fluorophenyl)ethyl | |
| 821 | 2-Propen-1-yl | 2-(4-Fluorophenyl)ethyl | |
| 822 | 2-Propen-1-yl | 2-(2-Chlorophenyl)ethyl | |
| 823 | 2-Propen-1-yl | 2-(4-Chlorophenyl)ethyl | |
| 824 | 2-Propen-1-yl | 2-(2,4-Dichlorophenyl)ethyl | |
| 825 | 2-Propen-1-yl | 2-(2-Chloro-4-fluorophenyl)ethyl | |
| 826 | 2-Propen-1-yl | 2-(4-Cyanophenyl)ethyl | |

-continued

| No. | R¹ | R² | Physical data |
|---|---|---|---|
| 827 | 2-Propen-1-yl | 2-(4-Hydroxyphenyl)ethyl | |
| 828 | 2-Propen-1-yl | 2-(4-Nitrophenyl)ethyl | |
| 829 | 2-Propen-1-yl | 3-Phenylpropyl | |
| 830 | 2-Propen-1-yl | 3-(4-Methylphenyl)propyl | |
| 831 | 2-Propen-1-yl | 3-(4-tert.-Butylphenyl)propyl | |
| 832 | 2-Propen-1-yl | 3-(2-Methoxyphenyl)propyl | |
| 833 | 2-Propen-1-yl | 3-(4-Methoxyphenyl)propyl | |
| 834 | 2-Propen-1-yl | 3-(3,4-Dimethoxyphenyl)propyl | |
| 835 | 2-Propen-1-yl | 3-(4-tert.-Butoxyphenyl)propyl | |
| 836 | 2-Propen-1-yl | 3-(3-Trifluoromethylphenyl)propyl | |
| 837 | 2-Propen-1-yl | 3-(4-Trifluoromethoxyphenyl)propyl | |
| 838 | 2-Propen-1-yl | 3-(2-Fluorophenyl)propyl | |
| 839 | 2-Propen-1-yl | 3-(4-Fluorophenyl)propyl | |
| 840 | 2-Propen-1-yl | 3-(2-Chlorophenyl)propyl | |
| 841 | 2-Propen-2-yl | 3-(4-Chlorophenyl)propyl | |
| 842 | 2-Propen-1-yl | 3-(2,4-Dichlorophenyl)propyl | |
| 843 | 2-Propen-1-yl | 3-(2-Chloro-4-fluorophenyl)propyl | |
| 844 | 2-Propen-1-yl | 3-(4-Cyanophenyl)propyl | |
| 845 | 2-Propen-1-yl | 3-(4-Hydroxyphenyl)propyl | |
| 846 | 2-Propen-1-yl | 3-(4-Nitrophenyl)propyl | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals.
*Rhizoctonia solani* in cotton,
Ustilago species in cereals and sugar cane,
*Venturia inaequalis* (scab) in apples.
Helminthosporium species in cereals,
*Septoria nodorum* in wheat,
*Botrytis cinerea* (gray mold) in strawberries and grapes,
*Cercospora arachidicoka* in groundnuts,
*Pseudocercosporella herpotrichoides* in wheat and barley,
*Pyricuiaria oryzae* in rice,
*Phytophthora infestans* in potatoes and tomatoes,
Fusarium and verticillium species in various plants,
*Plasmopara viticola* in grapes,
Alternaria species in fruit and vegetables, The compounds are applied by spraying or dusting the plants with the active ingredients, or treating the seeds of the plants with the active ingredients. They may be applied before or after infection of the plants or seeds by the fungi. Either the fungi themselves, or the plants, seeds, materials or the soil to be protected against fungus attack are treated with a fungicidally effective amount of the active ingredient.

The novel substances can be converted into conventional formulations such as solutions, emulsions, suspensions, dusts, powders, pastes and granules. The application forms depend entirety on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent it is also possible to employ other organic solvents as auxiliary solvents, suitable auxiliaries for this purpose are solvents such as aromatics (e.g., xylene), chlorinated aromatics (e.g., chlorobenzenes), paraffins (e.g., crude oil fractions). alcohols e.g., methanol, butanol), ketones e.g., cyclohexanone), amines e.g., ethanolamine, dimethylformamide), and water; carriers such as ground natural minerals e.g. kaolins, aluminas, talc and chalk) and ground synthetic minerals e.g., highly disperse silica and silicates; emulsifiers such as nonionic and anionic emulsifiers e.g., polyoxyethylene fatty alcohol ethers, alkyl sulfonates and aryl sulfonates); and dispersants such as ligninsulfite waste liquors and methylcellulose.

The fungicides generally contain from 0.1 to 95, and preferably from 0.5 to 90, wt% of active ingredient. The application rates are from 0.02 to 3 kg or more of active ingredient per hectare. depending on the type of effect desired. The novel compounds may also be used for protecting materials timber), e.g., on Paecilomyces variotii, when the active ingredients are used for treating seed, amounts of from 0.001 to 50, and preferably from 0.01 to 20, g per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 62 and 10 parts by weight of N-methyl-α-pyrrolidone, which is suitable for application in the form of very fine drops.

II. A mixture of 20 parts by weight of compound no. 5, 80 parts by weight of xylene. 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 15, 40 parts by weight of cyclohexanone, 30 parts by weight of isobutanol, 20 parts by weight of the adduct of 40 moles of ethylene oxide and 1 mole of castor oil. By finely dispersing this mixture in water, an aqueous dispersion of the active ingredient is obtained.

IV. An aqueous dispersion of 20 parts by weight of compound no. 39, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By finely distributing this mixture in water, an aqueous dispersion is obtained.

V. A hammer-milled mixture of 80 parts by weight of compound no. 123, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silca gel. By finely dispersing the mixture in water a spray liquor is obtained.

VI. An intimate mixture of 3 parts by weight of compound no. 50 and 97 parts by weight of particulate kaolin. The dust contains 3 wt% of the active ingredient.

VII. An intimate mixture of 30 parts by weight of compound no. 59, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 61, 10 parts of the sodium salt of a phenolsulfonic acid-urea-formaldehyde condensate. 2 parts of silica gel and 48 parts of water, which dispersion can be further diluted.

IX. A stable oily dispersion of 20 parts by weight of compound no. 67, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate.
zinc N,N'-propylenebisdithioccarbamate and N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-butylcarbamyl-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide.
N-trichloromethylthiophthalimide.

N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole
1,4-dichloro-2,5-dimethoxybenzene,
4-(2-chlorophenylhydrazono)-3-methyl-5-isoxazolone,
2-thiopyridine 1-oxide.
8-hydroxyquinoline and its copper salt,
2,3-dihydro-5-carboxanilido-6-methyl-1,4-oxathiyne,
2,3-dlhydro-5-carboxanilido-6-methyl-1,4-oxathlyne 4,4-dioxide,
2-methyl-5,6-dihydro-4H-pyran-3-carboxanilide.
2-methylfuran-3-carboxanilide,
2,5-dimethylfuran-3-carboxanilide,
2,4,5-trimethylfuran-3-carboxanilide.
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide,
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyli-piperidine,
1-[2-(2,4-dichlorophenyl)-4-ethyl-1,3-dioxolan-2-ylethyl]-1H-1,2,4-triazole.
1-[2-(2,4-dichlorophenyl)-4-n-propyl-1,3-dioxolan-2-ylethyl]-1H-1,2,4-triazole.
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl-butan-2-one,
1-(4-chlorophenoxy)-3,3-dimethyl-1-1H-1,2,4-triazol-1-yl-butan-2-ol,
α-(2-chlorophenyl)-α-(4-chlorophenyl)-5-pyrimidinemethanol,
5-butyl-(2-dimethylamino-4-hydroxy-6-methylpyrimidine, bis-(p-chlorophenyl)-3-pyridinemethanol,
1,2-bis-(3-ethoxycarbonyl-2-thioureido)-benzene.
1,2-bis-(3-methoxycarbonyl-2-thioureido)-benzene, and various fungicides, such as
dodecylguanidine acetate.
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate.
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl-1H-1,2,4-triazole.

USE EXAMPLES

For comparison purposes, 1-(4-(4-tert-butylphenyl)-cyclohexyl)-2,6-dimethylmorpholine (A) disclosed in EP 259,977, N,N-dimethyl-4-cyclohexylmethyl)-cyclohexylamine (B) and 4(cyclohexylmethyl)-cyclohexylamine (C), both disclosed in U.S. Pat. No. 3,981,766, and trans-4-tert-butyl-N-benzylcyclohexylamine (D) disclosed in Journal of Organic Chemistry, 48 (1983), pp. 3412-3422.

USE EAMPLES 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 5, 15, 39, 40, 50, 59, 61, 62 and 67, applied as 0.025 wt% spray liquors, have a better fungicidal action (100%) than prior art comparative agents A and C (75%).

USE EXAMPLES 2

Action on *Botrytis cinerea* in paprika

Paprika seedlings of the "Neusiedler Ideal Elite" variety were sprayed, after 4 to 5 leaves were well developed, to runoff witn aqueous suspensions containing dry basis 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results show that active ingredients 5, 15, 59, 61, 62 and 67, applied as 0.05% spray liquors, have a better fungicidal action (90%) than prior art active ingredients B, C and D (60%).

We claim:

1. A 4-(4-tert-butylphenyl-cyclohexylamine and quaternary ammonium salts thereof of the formulae

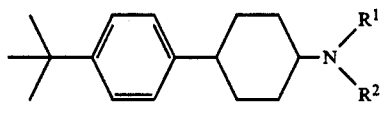

and

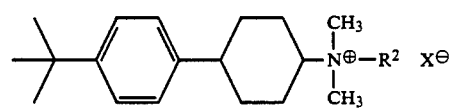

where
$R^1$ is hydrogen, $C_1$-$C_6$-alkyl or $C_3$-$C_6$-alkenyl,
$R^2$ is $C_1$-$C_{12}$-alkyl $C_1$-$C_{12}$-haloalkyl, $C_1$-$C_{12}$-hydroxyalkyl, $C_3$-$C_{12}$cycloalkyl, $C_4$-$C_{12}$-alkylcycloalkyl, $C_7$-$C_{12}$-bicycloalkyl, $C_3$-$C_{12}$-alkenyl, unsubstituted, monosubstituted, disubstituted or trisubstituted phenyl, or unsubstituted, monosubstituted, disubstituted or trisubstituted phenyl-($C_1$-$C_3$)alkyl, the substituents in each case being identical or different and being $C_1$-$C_4$-alkyl, $C_1$-$C_4$-alkoxy, $C_1$-$C_4$-haloalkyl, $C_1$-$C_4$-haloalkoxy, halogen, cyano, hydroxyl or nitro groups, with the proviso that $R^1$ and $R^2$ are not simultaneously $C_1$-$C_4$-alkyl,
$X^\ominus$ is a plant-tolerated acid anion,
and plant-tolerated acid addition salts thereof.

2. A fungicidal agent containing an inert carrier and a fungicidally effective amount of a 4-(4-tert-butylphenyl)-cyclohexylamine or a quaternary ammonium salt thereof of the formulae

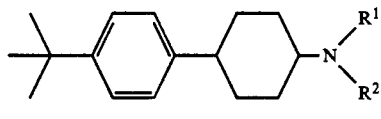

and

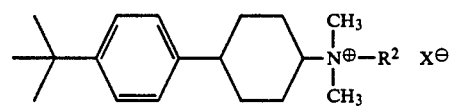

where
$R^1$ is hydrogen, $C_1$-$C_6$-alkyl or $C_3$-$C_6$-alkenyl,
$R^2$ is $C_1$-$C_{12}$-alkyl, $C_1$-$C_{12}$-haloalkyl, $C_1$-$C_{12}$-hydroxyalkyl, $C_3$-$C_{12}$-cycloalkyl, $C_4$-$C_{12}$-alkylcycloalkyl, $C_7$-$C_{12}$-bicycloalkyl, $C_3$-$C_{12}$-alkenyl, unsubstituted, monosubstituted, disubstituted or trisubstituted phenyl, or unsubstituted, monosubstituted, disubstituted or trisubstituted phenyl-($C_1$-$C_3$)alkyl, the substituents in each case being identical or different and being $C_1$-$C_4$-alkyl, $C_1$-$C_4$-alkoxy, $C_1$-$C_4$-haloalkyl, $C_1$-$C_4$-haloalkoxy, halogen, cyano, hydroxyl or nitro groups, with the proviso that $R^1$ and $R^2$ are not simultaneously $C_1$-$C_4$-alkyl, $X^\ominus$ is a plant-tolerated acid anion, or a plant-tolerated acid addition salt thereof.

3. A process for combating fungi, wherein the fungi or the plants, seed, materials or the soil to be protected against fungus attack are treated with a fungicidally effective amount of a 4-4-tert-butylphenyl-cyclohexylamine or a quaternary ammonium salt thereof of the formulae

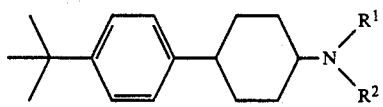

and

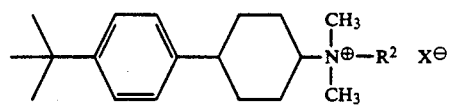

where $R^1$ is hydrogen, $C_1$-$C_6$-alkyl or $C_3$-$C_6$-alkenyl, $R^2$ is $C_1$-$C_{12}$-alkyl, $C_1$-$C_{12}$-haloalkyl, $C_1$-$C_2$-hydroxyalkyl, $C_3$-$C_{12}$-cycloalkyl, $C_4$-$C_{12}$-alkylcycloalkyl, $C_7$-$C_{12}$-bicycloalkyl, $C_3$-$C_{12}$-alkenyl, unsubstituted, monosubsiituted, disubstituted or trisubstituted phenyl, or unsubstituted, monosubstituted, disubstituted or trisubstituted phenyl-($C_1$-$C_3$)alkyl, the substituents in each case being identical or different and being $C_1$-$C_4$-alkyl, $C_1$-$C_4$-alkoxy, $C_1$-$C_4$-haloalkyl, $C_1$-$C_4$-haloalkoxy, halogen, cyano, hydroxyl or nitro groups, with the proviso that $R^1$ and $R^2$ are not simultaneously $C_1$-$C_4$-alkyl.

$X^\ominus$ is a plant-tolerated acid anion.

or a plant-tolerated acid addition salt thereof.

4. A compound of the formula 1 as set forth in claim 1, where $R^1$ is hydrogen and $R^2$ is 4-tert-butylcyclohexyl.

5. A compound of the formula 2 as set forth in claim 1, where $R^2$ is 4-tert-butylcyclohexyl and $X^\ominus$ is iodide.

6. A compound of the formula 1 as set forth in claim 1, where $R^1$ is hydrogen and $R^2$ is cyclohexyl.

7. A compound of the formula 1, as set forth in claim 1, wherein $R^1$ is methyl and $R^2$ is benzyl.

* * * * *